United States Patent
Kim et al.

(10) Patent No.: US 10,716,494 B2
(45) Date of Patent: Jul. 21, 2020

(54) METHOD OF PROVIDING INFORMATION ACCORDING TO GAIT POSTURE AND ELECTRONIC DEVICE FOR SAME

(71) Applicant: Samsung Electronics Co., Ltd., Suwon-si, Gyeonggi-do (KR)

(72) Inventors: Jeong-Bin Kim, Hwaseong-si (KR); Se-Hee Lee, Seoul (KR); Sung-Gook Kim, Seoul (KR); Tae-Hyun Kim, Seoul (KR); Soon-Seok Oh, Seoul (KR); Hyung-Jin Cho, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 486 days.

(21) Appl. No.: 15/146,336

(22) Filed: May 4, 2016

(65) Prior Publication Data
US 2016/0324445 A1    Nov. 10, 2016

(30) Foreign Application Priority Data

May 7, 2015 (KR) .......................... 10-2015-0064105
Jul. 21, 2015 (KR) .......................... 10-2015-0103150

(51) Int. Cl.
*A61B 5/11* (2006.01)
*A61B 5/103* (2006.01)
(Continued)

(52) U.S. Cl.
CPC .............. *A61B 5/112* (2013.01); *A43B 3/001* (2013.01); *A43B 3/0005* (2013.01);
(Continued)

(58) Field of Classification Search
CPC ....... A61B 5/112; A61B 5/4519; A61B 5/744; A61B 5/4528; A61B 5/6807; A61B 5/486;
(Continued)

(56) References Cited

U.S. PATENT DOCUMENTS

2005/0015002 A1* 1/2005 Dixon .................. A61B 5/1038
600/407
2011/0112808 A1* 5/2011 Anderson .............. G16H 50/50
703/2
(Continued)

FOREIGN PATENT DOCUMENTS

JP      2009-106386 A    5/2009
KR      10-0375712 B1    3/2003
(Continued)

OTHER PUBLICATIONS

Bamberg, et al. "Gait analysis using a shoe-integrated wireless sensor system." IEEE transactions on information technology in biomedicine 12.4 (2008): 413-423.*

(Continued)

*Primary Examiner* — David J. McCrosky
(74) *Attorney, Agent, or Firm* — Jefferson IP Law, LLP

(57) ABSTRACT

A method of providing information according to a gait posture and an electronic device for the same are provided. The method includes collecting sensor values detected using a plurality of sensors located at the surrounding of a user's feet, determining a user's gait posture by using the detected sensor values, and outputting at least one of information on the user's gait posture, information on muscle fatigue of the user according to the gait, information on joint fatigue of the user according to the gait, and information on a recommended exercise for the user based on the determined user's gait posture.

41 Claims, 33 Drawing Sheets

(51) Int. Cl.
  *A61B 5/00* (2006.01)
  *A43B 3/00* (2006.01)
  *G01C 22/00* (2006.01)
  *G01C 21/16* (2006.01)

(52) U.S. Cl.
  CPC .......... *A43B 3/0021* (2013.01); *A61B 5/1038* (2013.01); *A61B 5/1116* (2013.01); *A61B 5/4519* (2013.01); *A61B 5/4528* (2013.01); *A61B 5/486* (2013.01); *A61B 5/6802* (2013.01); *A61B 5/6807* (2013.01); *A61B 5/744* (2013.01); *G01C 21/16* (2013.01); *G01C 22/006* (2013.01); *A61B 2562/0219* (2013.01)

(58) Field of Classification Search
  CPC ... A61B 5/1038; A61B 5/6802; A61B 5/1116; A61B 2562/0219; A43B 3/001; A43B 3/0021; A43B 3/0005; G01C 22/006
  USPC .................................................. 600/300, 301
  See application file for complete search history.

(56) References Cited

U.S. PATENT DOCUMENTS

| | | |
|---|---|---|
| 2014/0031725 A1 | 1/2014 | Jeon |
| 2014/0159911 A1 | 6/2014 | Gray et al. |
| 2014/0323827 A1* | 10/2014 | Ahmed .............. A61B 5/02405 600/301 |
| 2015/0294481 A1* | 10/2015 | Sakaue .................. G06Q 50/22 382/103 |
| 2016/0353995 A1* | 12/2016 | Oleson ............... A61B 5/02055 |
| 2017/0055880 A1* | 3/2017 | Agrawal .............. A61B 5/1038 |
| 2017/0189752 A1* | 7/2017 | Mohrman .......... A63B 24/0006 |

FOREIGN PATENT DOCUMENTS

| | | |
|---|---|---|
| KR | 10-0651504 B1 | 11/2006 |
| KR | 10-2007-0100592 A | 10/2007 |
| KR | 10-2010-0093463 A | 8/2010 |
| KR | 10-1252634 B1 | 4/2013 |
| KR | 10-2013-0112082 A | 10/2013 |
| KR | 10-2014-0026594 A | 3/2014 |
| KR | 10-2014-0066341 A | 6/2014 |
| KR | 10-1458931 B1 | 11/2014 |

OTHER PUBLICATIONS

Dingwell, et al. "Technical Brief A Rehabilitation Treadmill With Software for Providing Real-Time Gait Analysis and Visual Feedback." (1996).*
Machine translation of KR 20000017765.*
Machine Translation of KR 20070100592.*
Korean Office Action dated Feb. 14, 2020, issued in Korean Patent Application No. 10-2016-0178891.

* cited by examiner

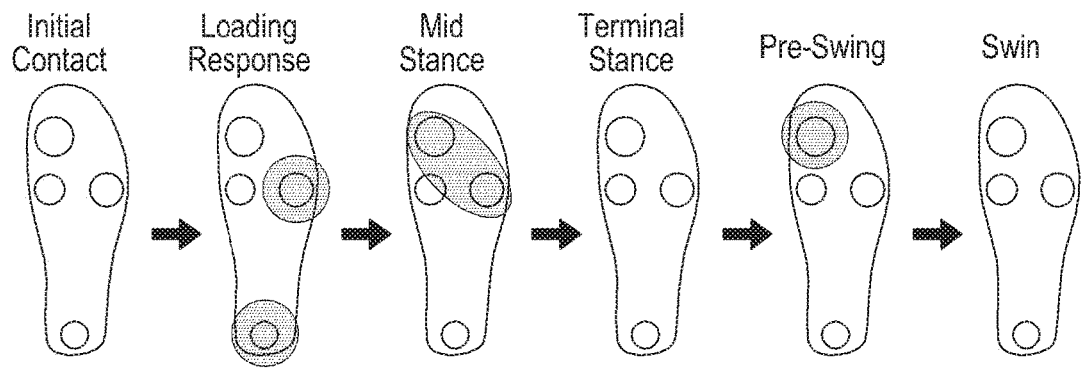
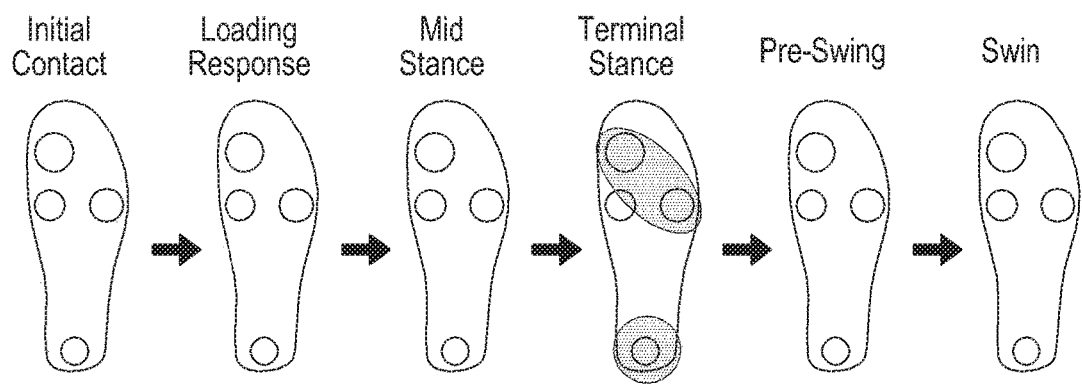
FIG.10A
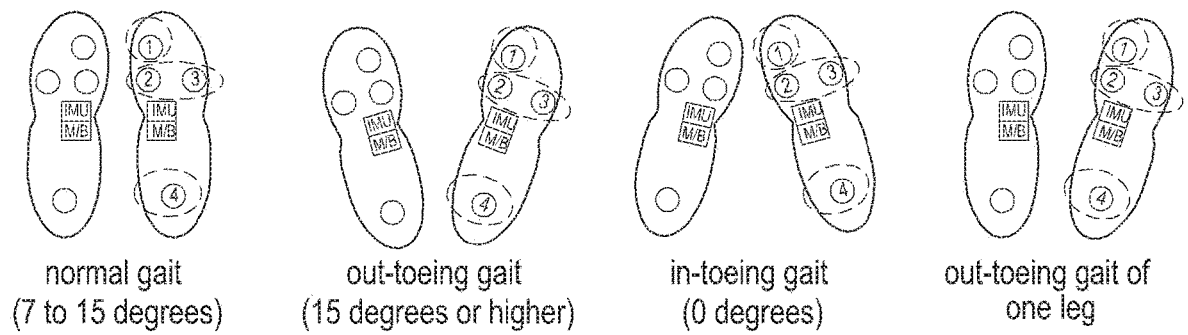
FIG.10B

| INPUT DATA | SCORE (intr) | ABNORMALITY REFERENCE | NAME |
|---|---|---|---|
| COG (X,Y COORDINATE) R = root(x*x + y*y) | POINTS FROM 50 TO 100 (s=100-2r) When 0≤r≤25 | NORMAL (s≥50) | STANDING |
| COG (X,Y COORDINATE) R = root(x*x + y*y) | POINTS FROM 0 TO 49 (s=100-2r) When 26≤r≤50 | ABNORMAL (0≤s≤49) | LEANING ON RIGHT FOOT ABNORMAL_ STANDING_R<br><br>LEANING ON LEFT FOOT ABNORMAL_ STANDING_L |

FIG.11A

| CLASSIFICATION | SCORE (intr) | NORMAL OR ABNORMAL | NAME |
|---|---|---|---|
| CROSSED LEGS | POINTS FROM 30 TO 0 (s=30-t/3) | ABNORMAL | RIGHT LEG-CROSSED ABNORMAL_ SITTING_R<br><br>LEFT LEG-CROSSED ABNORMAL_ SITTING_L |
| NO CROSSED LEGS (USE COG VALUE) | POINTS FROM 100 TO 30 (s=-1.4r+100) | NORMAL | SITTING |

FIG.11B

| INPUT DATA | | CLASSIFICATION | DATA RANGE(intr) | SCORE (INTS) | NORMAL OR ABNORMAL | NAME |
|---|---|---|---|---|---|---|
| IN-TOEING/ OUT-TOEING/ NORMALITY | | OUT-TOEING GAIT | 60~100% (a) | 50~0. (s=-1.25a+125) | ABNORMAL | ABNORMAL_ WALKING1 |
| | | IN-TOEING GAIT | 0~40% (a) | 50~0. (s=-1.25a) | ABNORMAL | ABNORMAL_ WALKING2 |
| | | NO OUT-TOEING NO IN-TOEING | 41~59% (a) | PERFORM DETERMINATION BASED ON GAIT NORMALITY | | |
| GAIT NORMALITY | | NORMAL GAIT | 100~51% (n) | 100~51. (s=n) | NORMAL | WALKING |
| | | ABNORMAL GAIT | 50~0% (n) | 50~0. (s=n) | ABNORMAL | ABNORMAL_ WALKING3 |

FIG. 11C

PRESSURE CHANGE

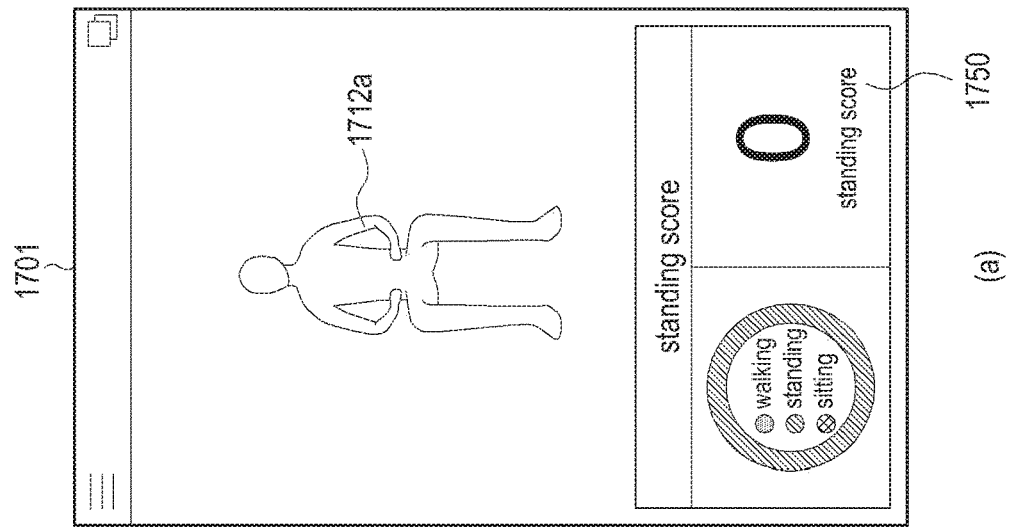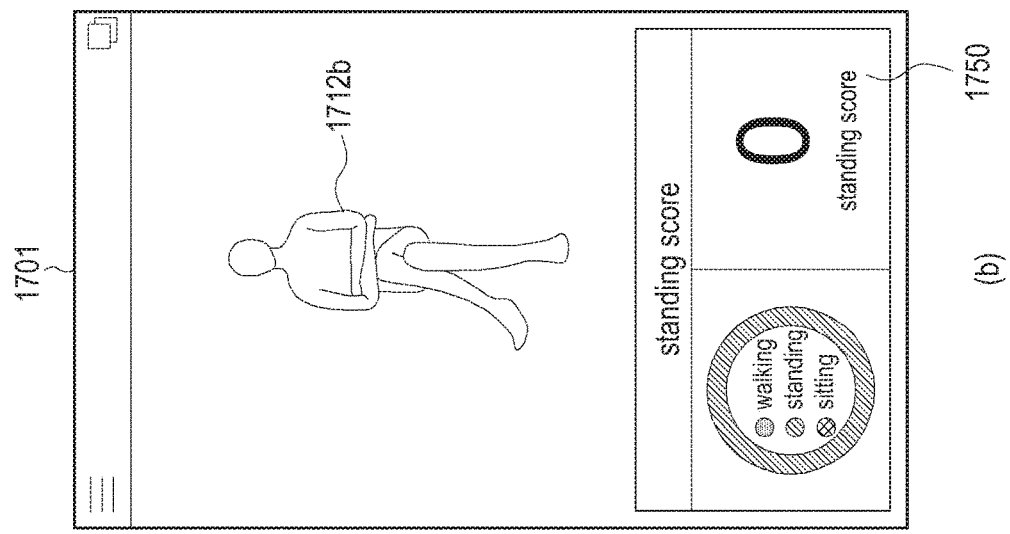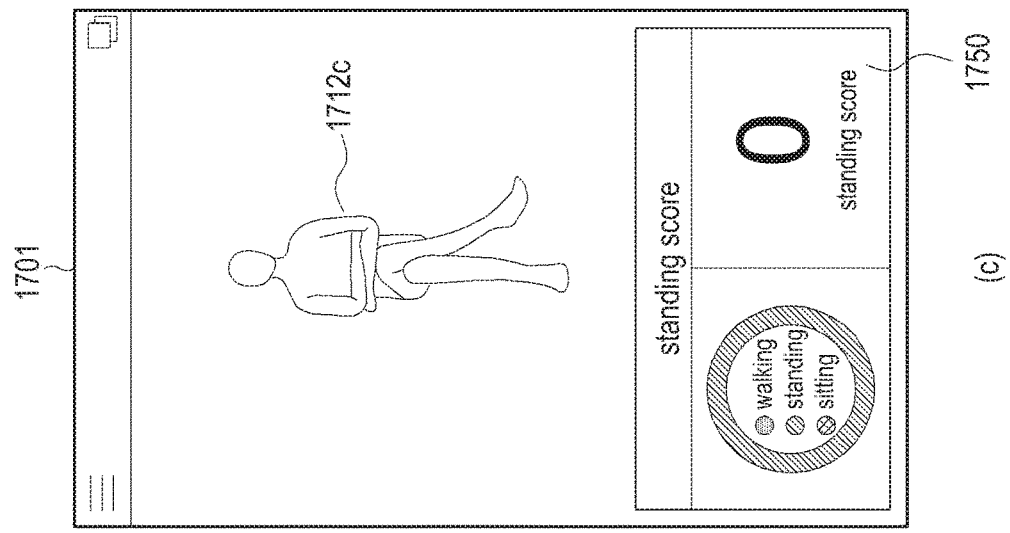
FIG.17C

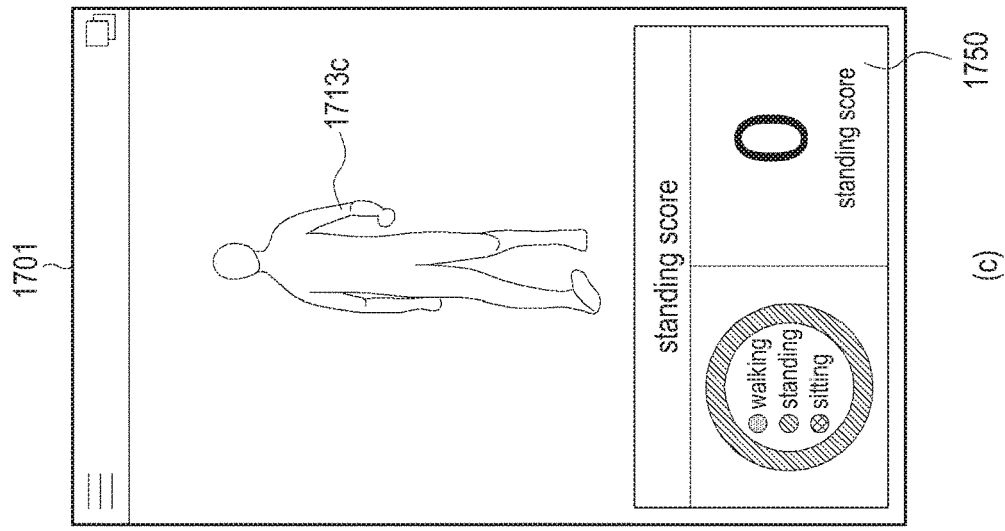
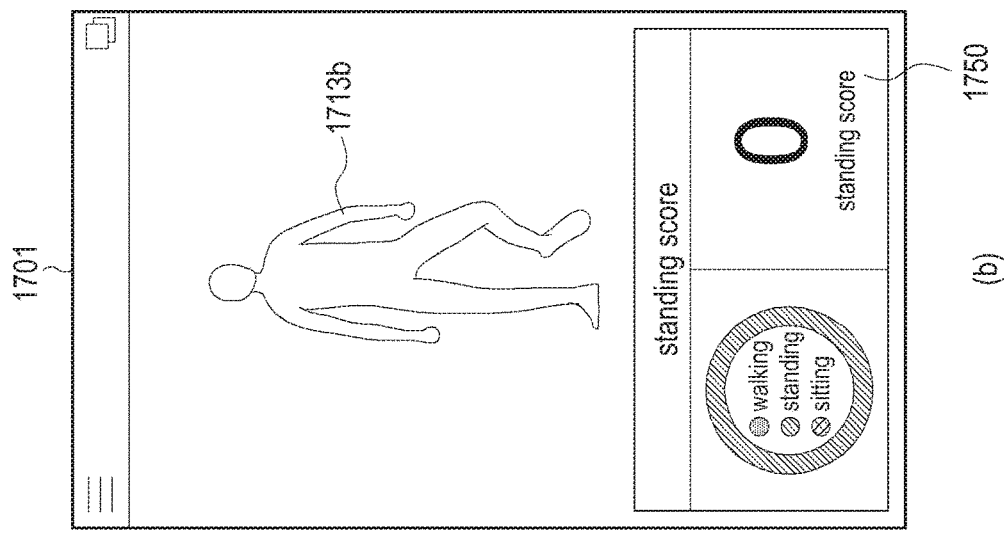
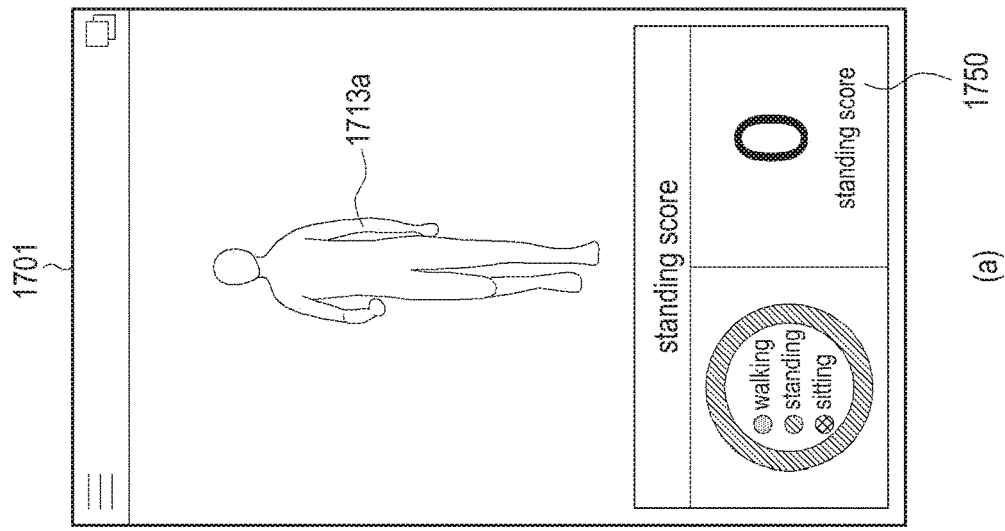
FIG.17D

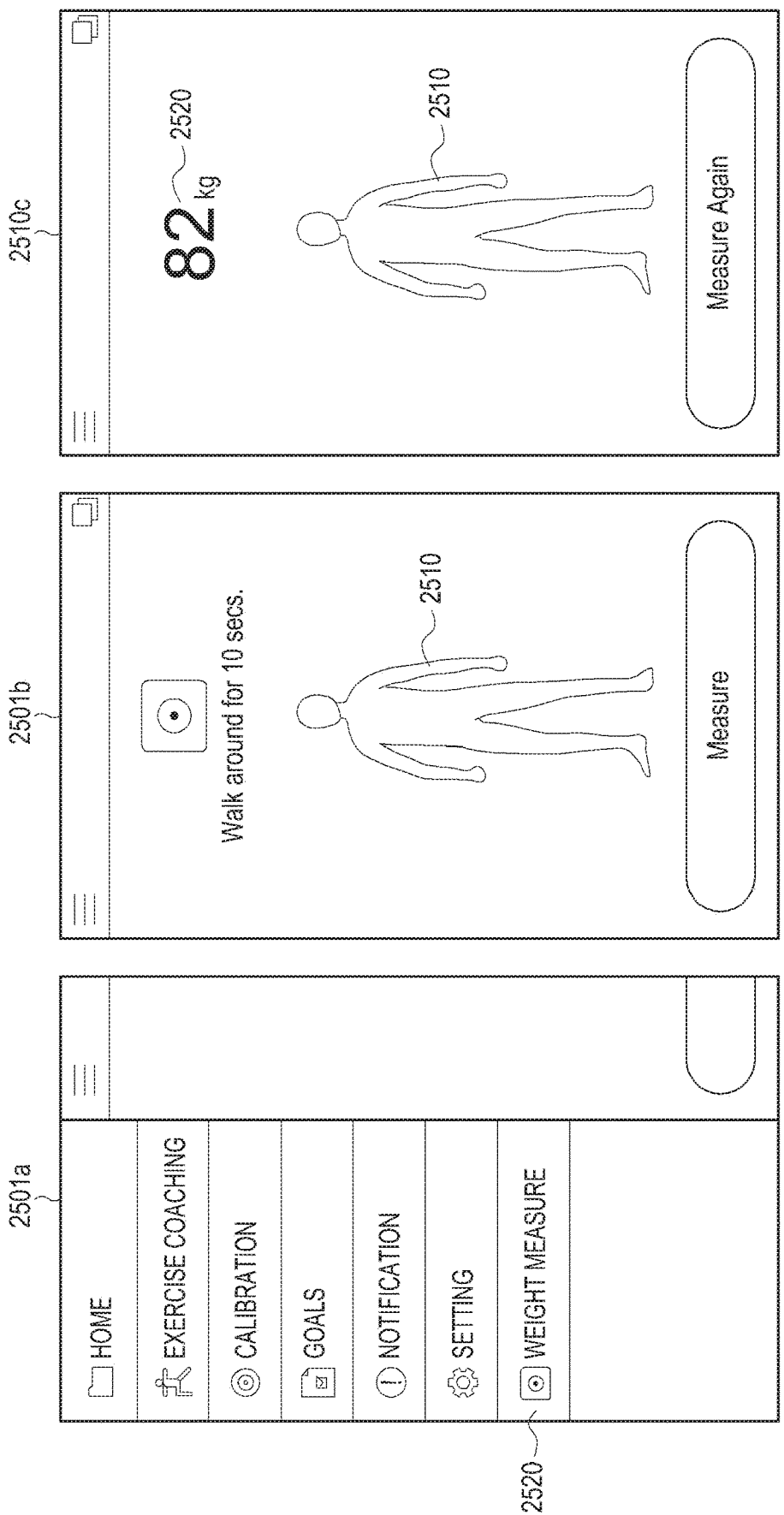

METHOD OF PROVIDING INFORMATION ACCORDING TO GAIT POSTURE AND ELECTRONIC DEVICE FOR SAME

CROSS-REFERENCE TO RELATED APPLICATION(S)

This application claims the benefit under 35 U.S.C. § 119(a) of a Korean patent application filed on May 7, 2015 in the Korean Intellectual Property Office and assigned Serial number 10-2015-0064105, and of a Korean patent application filed on Jul. 21, 2015 in the Korean Intellectual Property Office and assigned Serial number 10-2015-0103150, the entire disclosure of each of which is hereby incorporated by reference.

TECHNICAL FIELD

The present disclosure relates to a method of providing information according to a gait posture and an electronic device for the same. More particularly, the present disclosure relates to a method of providing information according to a gait posture and an electronic device for the same, which may determine a user's gait posture by multi-directionally measuring a user's gait, provide information on the determined user's gait posture in real time, and provide information on a user's muscle and joint fatigue and information on a recommended exercise for the user based on the user's gait posture.

BACKGROUND

A gait refers to a way of moving a body using a human's body part, and may be divided into walking and running according to a movement speed of the body and a ground contact type. Walking refers to a gait type having a double support phase in which both legs touch the ground, and running refers to a gait type having no double support phase since the center of gravity rapidly moves.

People walk or run almost every day in their daily life, and these days intentionally walk or run a long distance for health. However, every person has different gait postures. Body postures while walking or running vary and speeds or movement traces of feet vary from person to person.

A proper gait posture is important for not only young people in a period of growth but also adults. An improper gait posture may have a bad influence on growth and body types of the young people, and may even damage adults' health if they walk or run with an improper posture for a long time.

Recently, electronic devices include various sensors and gradually expand additional functions for providing information on a user's gait speed, a movement distance, and burnt calories through the sensors.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method of providing information according to a gait posture and an electronic device for the same, which may determine a user's gait posture by multi-directionally measuring a user's gait, provide information on the determined user's gait posture in real time, and provide information on a user's muscle and joint fatigue and information on a recommended exercise for the user based on the user's gait posture.

In accordance with an aspect of the present disclosure, a method of providing information according to a gait posture using an electronic device is provided. The method includes collecting sensor values detected using a plurality of sensors located around a user's feet, determining a user's gait posture by using the detected sensor values, and outputting at least one of information on the user's gait posture, information on muscle fatigue of the user according to the gait, information on joint fatigue of the user according to the gait, and information on a recommended exercise for the user based on the determined user's gait posture.

In accordance with another aspect of the present disclosure, an electronic device for providing information according to a gait posture is provided. The electronic device includes a pad part located at a user's sole, a plurality of sensors located within the pad part, a controller configured to control transmission of sensor values acquired by the plurality of sensors, and a communication unit configured to transmit the sensor values to an external electronic device by using short range communication.

According to various embodiments of the present disclosure, the present disclosure can provide a method of providing information according to a gait posture and an electronic device for the same, so as to determine a user's gait posture by multi-directionally measuring a user's gait, provide information on the determined user's gait posture in real time, and provide information on a user's muscle and joint fatigue and information on a recommended exercise for the user based on the user's gait posture.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 10A and 10B illustrate a method of determining a gait posture according to various embodiments of the present disclosure;

FIGS. 11A to 11C illustrate a method of determining a gait posture according to various embodiments of the present disclosure;

FIGS. 17A to 17E illustrate screens for providing information according to a gait posture according to various embodiments of the present disclosure;

FIGS. 25A to 25C illustrate screens for providing body information by using an electronic device according to various embodiments of the present disclosure.

Throughout the drawings, it should be noted that like reference numbers are used to depict the same or similar elements, features, and structures.

DETAILED DESCRIPTION

Figure 1:
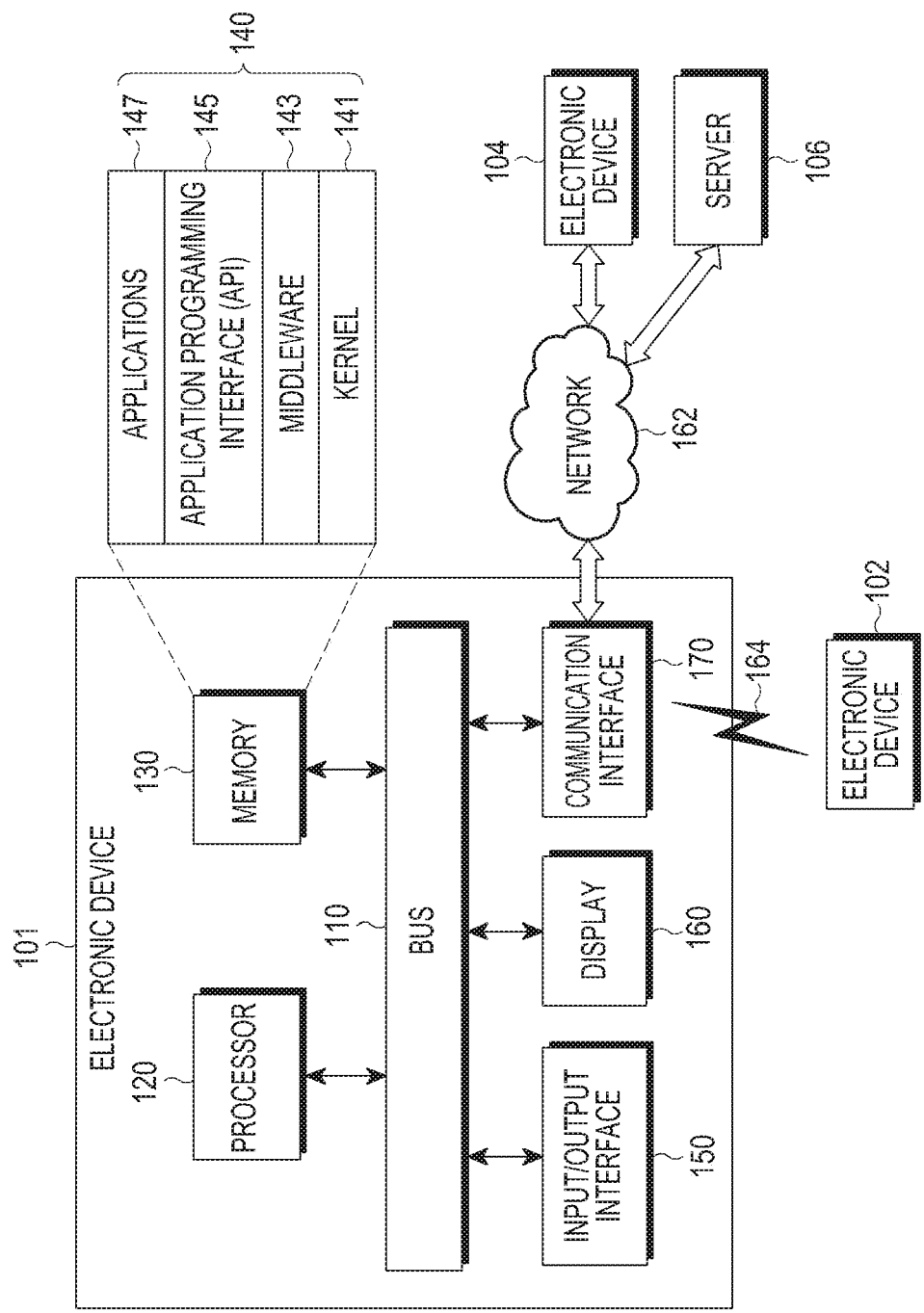
FIG. 1 is a block diagram illustrating an electronic device within a network environment according to various embodiments of the present disclosure.

The following description with reference to the accompanying drawings is provided to assist in a comprehensive understanding of various embodiments the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the expression "have", "may have", "include", or "may include" refers to the existence of a corresponding feature (e.g., a numeral, a function, an operation, or a constituent element, such as a component), and does not exclude one or more additional features.

In an embodiment of the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in embodiments of the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g., an embedded processor) only for performing the corresponding operations or a generic-purpose processor (e.g., a central processing unit (CPU) or an application processor (AP)) that can perform the corresponding operations by executing one or more software programs stored in a memory device.

Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device, according to various embodiments of the present disclosure, may include at least one of, for example, a smart phone, a tablet personal computer (PC), a mobile phone, a video phone, an electronic book reader (e-book reader), a desktop PC, a laptop PC, a netbook computer, a workstation, a server, a personal digital assistant (PDA), a portable multimedia player (PMP), a moving picture experts group phase 1 or phase 2 (MPEG-1 or MPEG-2) audio layer-3 (MP3) player, a mobile medical device, a camera, and a wearable device. According to various embodiments of the present disclosure, the wearable device may include at least one of an accessory type (e.g., a watch, a ring, a bracelet, an anklet, a necklace, a glasses, a contact lens, a head-mounted device (HMD), and the like), a fabric or clothing integrated type (e.g., an electronic clothing), a body-mounted type (e.g., a skin pad, or tattoo), and a bio-implantable type (e.g., an implantable circuit).

According to various embodiments of the present disclosure, the electronic device may be a home appliance. The home appliance may include at least one of, for example, a television (TV), a digital versatile disc (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to an embodiment of the present disclosure, the electronic device may include at least one of various medical devices (e.g., various portable medical measuring devices (a blood glucose monitoring device, a heart rate monitoring device, a blood pressure measuring device, a body temperature measuring device, and the like), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight data recorder (FDR), a vehicle infotainment device, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, and the like).

According to various embodiments of the present disclosure, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device, according to various embodiments of the present disclosure, may be a combination of one or more of the aforementioned various devices. The electronic device, according to various embodiments of the present disclosure, may be a flexible device. Further, the electronic device according to an embodiment of the present disclosure is not limited to the aforementioned devices, and may include a new electronic device according to the development of technology.

Hereinafter, an electronic device according to various embodiments of the present disclosure will be described with reference to the accompanying drawings. As used herein, the term "user" may indicate a person who uses an electronic device or a device (e.g., an artificial intelligence electronic device) that uses an electronic device.

FIG. 1 is a block diagram illustrating an electronic device within a network environment according to various embodiments of the present disclosure.

Referring to FIG. 1, an electronic device 101 may include a bus 110, a processor 120, a memory 130, an input/output interface 150, a display 160, and a communication interface 170. In various embodiments of the present disclosure, the electronic device 101 may omit at least some of the above elements or further include other elements.

The bus 110 may include a circuit for connecting the elements and transmitting communication between the elements (for example, control messages and/or data).

The processor 120 may include one or more of a CPU, an AP, and a communications processor (CP). The processor 120 may carry out, for example, operations or data processing related to control and/or communication of one or more other elements of the electronic device 101.

The memory 130 may include a volatile memory and/or a non-volatile memory. The memory 130 may store, for example, instructions or data relevant to at least one other element of the electronic device 101. According to an embodiment of the present disclosure, the memory 140 may store software and/or a program 150. The program 140 may include a kernel 141, middleware 143, an application programming interface (API) 145, and/or an application program (or "application") 147. At least some of the kernel 141, the middleware 143, and the API 145 may be referred to as an operating system (OS).

The kernel 141 may control or manage system resources (for example, the bus 110, the processor 120, or the memory 130) used for performing an operation or function implemented by the other programs (for example, the middleware 143, the API 145, or the application programs 147). Furthermore, the kernel 141 may provide an interface through which the middleware 143, the API 145, or the application programs 147 may access the individual elements of the electronic device 101 to control or manage the system resources.

The middleware 143 may function as, for example, an intermediary for allowing the API 145 or the application programs 147 to communicate with the kernel 141 to exchange data.

In addition, the middleware 143 may process one or more task requests received from the application programs 147 according to priorities thereof. For example, the middleware 143 may assign priorities for using the system resources (for example, the bus 110, the processor 120, the memory 130, and the like) of the electronic device 101, to at least one of the application programs 147. For example, the middleware 143 may perform scheduling or load balancing on the one or more task requests by processing the one or more task requests according to the priorities assigned thereto.

The API 145 is an interface through which the applications 147 control functions provided from the kernel 141 or the middleware 143, and may include, for example, at least one interface or function (for example, instruction) for file control, window control, image processing, or text control.

The input/output interface 150 may function as, for example, an interface that may transfer instructions or data input from a user or another external device to the other element(s) of the electronic device 101. In addition, the input/output interface 150 may output instructions or data received from other element(s) of the electronic device 101 to the user or another external device.

The display 160 may include, for example, a liquid crystal display (LCD), a light-emitting diode (LED) display, an organic LED (OLED) display, a microelectromechanical systems (MEMS) display, and an electronic paper display. The display 160 may display, for example, various types of contents (for example, a text, images, videos, icons, symbols, and the like) to users. The display 160 may include a touch screen and receive, for example, a touch, a gesture, proximity, or a hovering input using an electronic pen or the user's body part.

The communication interface 170 may establish communication between, for example, the electronic device 101 and an external device (for example, a first external electronic device 102, a second external electronic device 104, or a server 106). For example, the communication interface 170 may be connected to a network 162 through wireless or wired communication to communicate with the external device (for example, the second external electronic device 104 or the server 106).

The wireless communication may use at least one of, for example, long term evolution (LTE), LTE-advanced (LTE-A), code division multiple access (CDMA), wideband CDMA (WCDMA), universal mobile telecommunications system (UMTS), wireless broadband (WiBro), and global system for mobile communications (GSM), as a cellular communication protocol. In addition, the wireless communication may include, for example, a short range communication 164. The short-range communication 164 may be performed by using at least one of, for example, Wi-Fi, BLUETOOTH (BT), near field communication (NFC), and global navigation satellite system (GNSS). The GNSS may include at least one of, for example, a GPS, a global navigation satellite system (GLONASS), a BeiDou navigation satellite system (hereinafter referred to as "BeiDou"), and a European global satellite-based navigation system (Galileo), according to a use area, a bandwidth, and the like. Hereinafter, in the present disclosure, the "GPS" may be interchangeably used with the "GNSS". The wired communication may include, for example, at least one of a universal serial bus (USB), a high definition multimedia interface (HDMI), recommended standard 232 (RS-232), and a plain old telephone service (POTS). The network 162 may include at least one of a telecommunication network, for example, a computer network (for example, a local access network (LAN) or a wide access network (WAN)), the Internet, and a telephone network.

Each of the first external electronic device 102 and the second external electronic device and the second external electronic device 104 may be of a type identical to or different from that of the electronic device 101. According to an embodiment of the present disclosure, the server 106 may include a group of one or more servers. According to various embodiments of the present disclosure, all or some of the operations performed by the electronic device 101 may be performed by another electronic device or a plurality of electronic devices (for example, the first external electronic device 102 or the second external electronic device 104 or the server 106). According to an embodiment of the present disclosure, when the electronic device 101 should perform some functions or services automatically or by request, the electronic device 101 may make a request for performing at least some of the functions related to the functions or services to another device (for example, the first external electronic device 102 or the second external electronic device 104 or the server 106) instead of performing the functions or services by itself. Another electronic device (for example, the first external electronic device 102 or the second external electronic device 104) may execute the requested functions or the additional functions, and may deliver a result of the execution to the electronic device 101. The electronic device 101 may process the received result as it is or additionally to provide the requested functions or services. To achieve this, for example, cloud computing, distributed computing, or client-server computing technology may be used.

Figure 2:
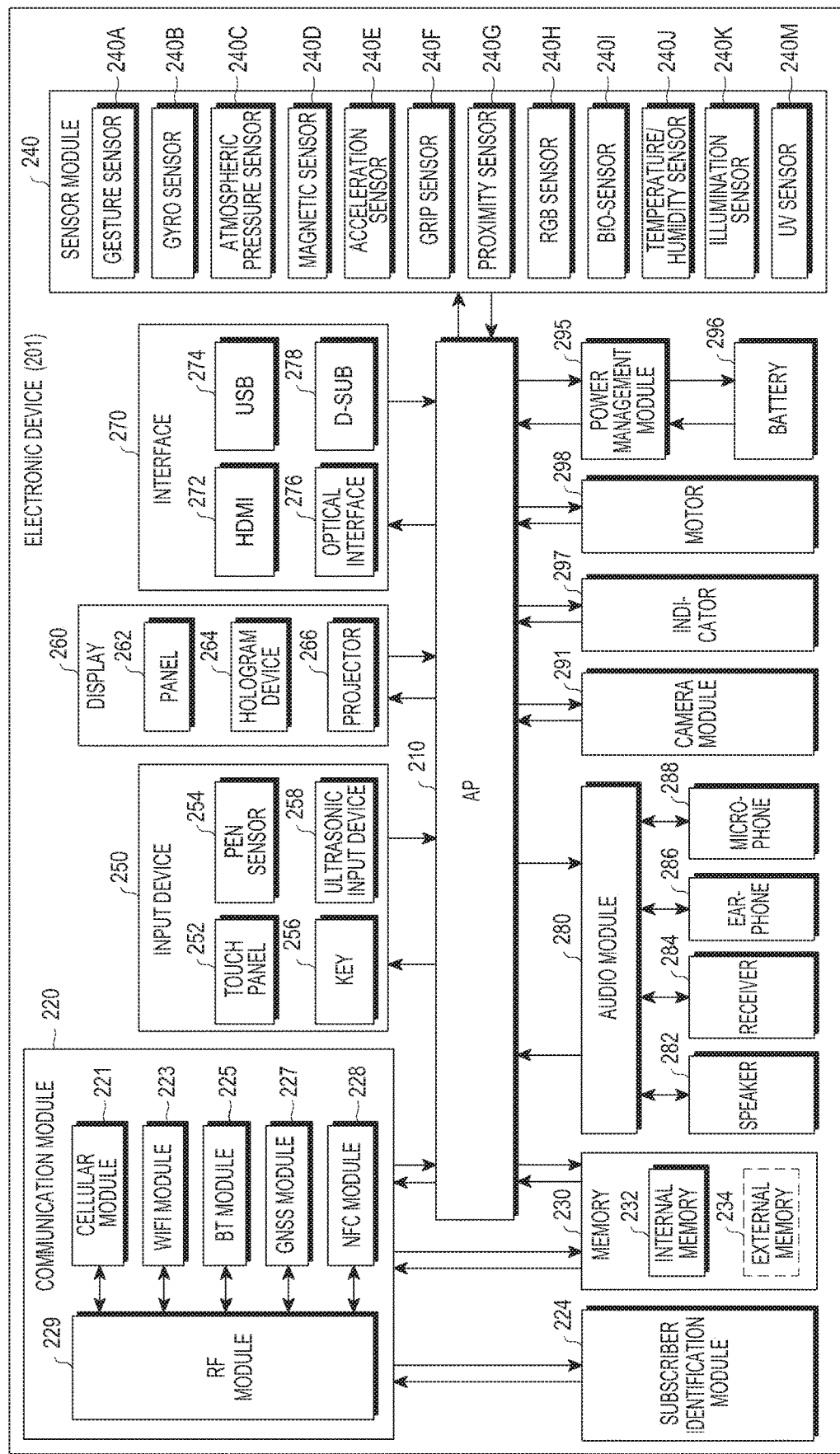
FIG. 2 is a block diagram illustrating an electronic device according to various embodiments of the present disclosure.

FIG. 2 is a block diagram illustrating an electronic device according to various embodiments of the present disclosure.

Referring to FIG. 2, an electronic device 201 may include, for example, the whole or part of the electronic device 101 illustrated in FIG. 1. The electronic device 201 may include one or more APs 210, a communication module 220, a subscriber identification module 224, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an OS or an application program and perform processing of various pieces of data and calculations. The processor 210 may be implemented by, for example, a system on chip (SoC). According to an embodiment of the present disclosure, the processor 210 may further include a graphics processing unit (GPU) and/or an image signal processor (ISP). The processor 210 may include at least some (for example, a cellular module 221) of the elements illustrated in FIG. 2. The processor 210 may load, into a volatile memory, instructions or data received from at least one (for example, a non-volatile memory) of the other elements and may process the loaded instructions or data, and may store various data in a non-volatile memory.

The communication module 220 may have a configuration equal or similar to that of the communication interface 170 of FIG. 1. The communication module 220 may include, for example, the cellular module 221, a Wi-Fi module 223, a BT module 225, a GNSS module 227, an NFC module 228, and a radio frequency (RF) module 229.

The cellular module 221 may provide a voice call, an image call, a text message service, or an Internet service through, for example, a communication network. According to an embodiment of the present disclosure, the cellular module 221 may identify and authenticate the electronic device 201 within a communication network using a subscriber identification module (SIM, for example, the SIM card 224). According to an embodiment of the present disclosure, the cellular module 221 may perform at least some of the functions that the processor 210 may provide. According to an embodiment of the present disclosure, the cellular module 221 may include a CP.

Each of the Wi-Fi module 223, the BT module 225, the GNSS module 227, and the NFC module 228 may include, for example, a processor for processing data transmitted and received through the relevant module. According to various embodiments of the present disclosure, at least some (for example, two or more) of the cellular module 221, the Wi-Fi module 223, the BT module 225, the GNSS module 227, and the NFC module 228 may be included in one integrated chip (IC) or IC package.

The RF module 229 may transmit/receive, for example, a communication signal (for example, an RF signal). The RF module 229 may include, for example, a transceiver, a power amp module (PAM), a frequency filter, a low noise amplifier (LNA), or an antenna. According to an embodiment of the present disclosure, at least one of the cellular module 221, the Wi-Fi module 223, the BT module 225, the GNSS module 227, and the NFC module 228 may transmit and receive RF signals through a separate RF module.

The subscriber identification module 224 may include, for example, a card including a subscriber identity module and/or an embedded SIM, and may contain unique identification information (for example, an integrated circuit card identifier (ICCID)) or subscriber information (for example, an international mobile subscriber identity (IMSI)).

The memory 230 (for example, the memory 130) may include, for example, an internal memory 232 or an external memory 234. The internal memory 232 may include at least one of a volatile memory (for example, a dynamic random access memory (DRAM), a static RAM (SRAM), a synchronous dynamic RAM (SDRAM), and the like) and a non-volatile memory (for example, a one time programmable read only memory (OTPROM), a programmable ROM (PROM), an erasable and programmable ROM (EPROM), an electrically erasable and programmable ROM (EEPROM), a mask ROM, a flash ROM, a flash memory (for example, a NAND flash memory or a NOR flash memory), a hard disk drive, a solid state drive (SSD), and the like).

The external memory 234 may further include a flash drive, for example, a compact flash (CF), a secure digital (SD), a micro-SD, a mini-SD, an extreme digital (xD), a memory stick, and the like. The external memory 234 may be functionally and/or physically connected to the electronic device 201 through various interfaces.

The sensor module 240 may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (for example, a red, green, blue (RGB) sensor), a biometric sensor 240I, a temperature/humidity sensor 240J, a light sensor 240K, and an ultraviolet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 240 may further include a control circuit for controlling one or more sensors included therein. According to various embodiments of the present disclosure, the electronic device 201 may further include a processor configured to control the sensor module 240 as a part of or separately from the AP 210, and may control the sensor module 240 while the AP 210 is in a sleep state.

The input device 250 may include, for example, a touch panel 252, a (digital) pen sensor 254, a key 256, and an ultrasonic input unit 258. The touch panel 252 may use at least one of, for example, a capacitive type, a resistive type, an IR type, and an ultrasonic type. In addition, the touch panel 252 may further include a control circuit. The touch panel 252 may further include a tactile layer and provide a tactile reaction to the user.

The (digital) pen sensor 254 may include, for example, a recognition sheet which is a part of the touch panel or is separated from the touch panel. The key 256 may include, for example, a physical button, an optical key or a keypad. The ultrasonic input unit 258 may input data through an input unit that generates an ultrasonic signal, and the electronic device 201 identify data by detecting a sound wave with a microphone (for example, a microphone 288).

The display 260 (for example, the display 160) may include a panel 262, a hologram device 264 or a projector 266. The panel 262 may include a configuration identical or similar to that of the display 160 illustrated in FIG. 1. The panel 262 may be implemented to be, for example, flexible, transparent, or wearable. The panel 262 and the touch panel 252 may be implemented as one module. The hologram 264 may show a three dimensional image in the air by using an interference of light. The projector 266 may display an image by projecting light onto a screen. The screen may be located, for example, inside or outside the electronic device 201. According to an embodiment of the present disclosure, the display 260 may further include a control circuit for controlling the panel 262, the hologram device 264, or the projector 266.

The interface 270 may include, for example, an HDMI 272, a USB 274, an optical interface 276, or a D-subminiature (D-sub) 278. The interface 270 may be included in, for example, the communication interface 170 illustrated in FIG. 1. Additionally or alternatively, the interface 270 may, for example, include a mobile high-definition link (MHL) interface, an SD card/multi-media card (MMC) interface, or an infrared data association (IrDA) interface.

The audio module 280 may bilaterally convert, for example, a sound and an electrical signal. At least some elements of the audio module 280 may be included in, for example, the input/output interface 150 illustrated in FIG. 1. The audio module 280 may process sound information which is input or output through, for example, a speaker 282, a receiver 284, earphones 286, the microphone 288, and the like.

The camera module 291 is a device which may photograph a still image and a dynamic image. According to an embodiment of the present disclosure, the camera module 291 may include one or more image sensors (for example, a front sensor or a back sensor), a lens, an ISP or a flash (for example, LED or xenon lamp).

The power management module 295 may manage, for example, power of the electronic device 201. According to an embodiment of the present disclosure, the power management module 295 may include a power management IC (PMIC), a charger IC, or a battery or fuel gauge. The PMIC may use a wired and/or wireless charging method. Examples of the wireless charging method may include, for example, a magnetic resonance method, a magnetic induction method, an electromagnetic method, and the like. Additional circuits (for example, a coil loop, a resonance circuit, a rectifier, and the like) for wireless charging may be further included. The battery gauge may measure, for example, a residual quantity of the battery 296, and a voltage, a current, or a temperature during the charging. The battery 296 may include, for example, a rechargeable battery and/or a solar battery.

The indicator 297 may display a particular state (for example, a booting state, a message state, a charging state, and the like) of the electronic device 201 or a part (for example, the processor 210) of the electronic device 201. The motor 298 may convert an electrical signal into mechanical vibration, and may generate vibration, a haptic effect, and the like. Although not illustrated, the electronic device 201 may include a processing unit (for example, a GPU) for supporting a mobile TV. The processing unit for supporting mobile TV may, for example, process media data according to a certain standard, such as digital multimedia broadcasting (DMB), digital video broadcasting (DVB), or MediaFlo™.

Each of the above-described component elements of hardware, according to the present disclosure, may be configured with one or more components, and the names of the corresponding component elements may vary based on the type of electronic device. The electronic device, according to various embodiments of the present disclosure, may include at least one of the aforementioned elements. Some elements may be omitted or other additional elements may be further included in the electronic device. Further, some of the components of the electronic device, according to the various embodiments of the present disclosure, may be combined to form a single entity, and thus, may equivalently execute functions of the corresponding elements prior to the combination.

Figure 3:
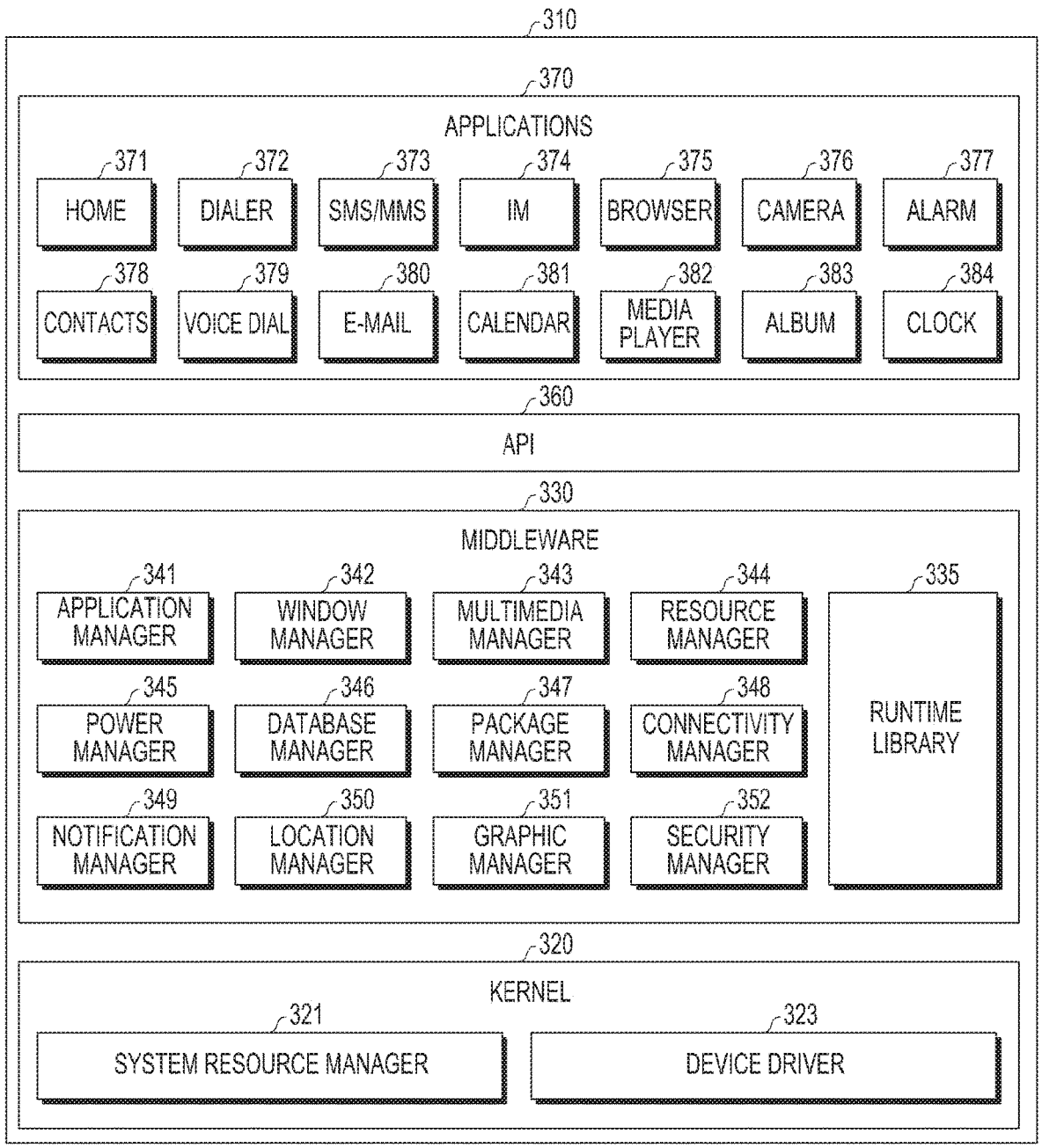
FIG. 3 is a block diagram illustrating a program module according to various embodiments of the present disclosure.

FIG. 3 is a block diagram illustrating a program module according to various embodiments of the present disclosure.

Referring to FIG. 3, according to an embodiment of the present disclosure, a program module 310 (for example, the program 140) may include an OS for controlling resources related to the electronic device (for example, the electronic device 101) and/or various applications (for example, the application programs 147) executed in the OS. The OS may be, for example, Android, iOS, Windows, Symbian, Tizen, Bada, and the like.

The program module 310 may include a kernel 320, middleware 330, an API 360, and/or applications 370. At least some of the program module 310 may be preloaded on the electronic device, or may be downloaded from an external electronic device (for example, the first external electronic device 102 or the second external electronic device 104, or the server 106).

The kernel 320 (for example, the kernel 141 of FIG. 1) may include, for example, a system resource manager 321 or a device driver 323. The system resource manager 321 may perform the control, allocation, retrieval, and the like, of system resources. According to an embodiment of the present disclosure, the system resource manager 321 may include a process manager, a memory manager, a file system manager, and the like. The device driver 323 may include, for example, a display driver, a camera driver, a BT driver, a shared memory driver, a USB driver, a keypad driver, a Wi-Fi driver, an audio driver, or an inter-process communication (IPC) driver.

The middleware 330 may provide a function required by the applications 370 in common or provide various functions to the applications 370 through the API 360 so that the applications 370 can efficiently use limited system resources within the electronic device. According to an embodiment of the present disclosure, the middleware 330 (for example, the middleware 143) may include, for example, at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module which a compiler uses in order to add a new function through a programming language while the applications 370 are being executed. The runtime library 335 may perform input/output management, memory management, the functionality for an arithmetic function, and the like.

The application manager 341 may manage, for example, a life cycle of at least one of the applications 370. The window manager 342 may manage graphical user interface (GUI) resources used for the screen. The multimedia manager 343 may determine a format required to reproduce various media files, and may encode or decode a media file by using a coder/decoder (codec) appropriate for the corresponding format. The resource manager 344 may manage resources, such as a source code, a memory, and a storage space of at least one of the applications 370.

The power manager 345 may operate together with a basic input/output system (BIOS) to manage a battery or power, and may provide power information required for the operation of the electronic device. The database manager 346 may generate, search for, and/or change a database to be used by at least one of the applications 370. The package manager 347 may manage the installation or update of an application distributed in the form of a package file.

The connectivity manager 348 may manage a wireless connection, such as, for example, Wi-Fi or BT. The notification manager 349 may display or notify of an event, such as an arrival message, an appointment, a proximity notification, and the like, in such a manner as not to disturb the user. The location manager 350 may manage location information of the electronic device. The graphic manager 351 may manage a graphic effect, which is to be provided to the user, or a user interface related to the graphic effect. The security manager 352 may provide various security functions required for system security, user authentication, and the like. According to an embodiment of the present disclosure, when the electronic device (for example, the electronic device 101) has a telephone call function, the middleware 330 may further include a telephony manager for managing a voice call function or a video call function of the electronic device.

The middleware 330 may include a middleware module that forms a combination of various functions of the above-described elements. The middleware 330 may provide a module specialized for each type of OS in order to provide a differentiated function. In addition, the middleware 330 may dynamically delete some of the existing elements, or may add new elements.

The API 360 (for example, the API 145) is, for example, a set of API programming functions, and may be provided with a different configuration according to an OS. For example, with respect to each platform, one API set may be provided in a case of Android or iOS, and two or more API sets may be provided in a case of Tizen.

The applications 370 (for example, the application programs 147) may include, for example, one or more applications which can provide functions, such as a home application 371, a dialer application 372, a short message service (SMS)/multimedia message service (MIMS) application 373, an instant message (IM) application 374, a browser application 375, a camera application 376, an alarm application 377, contacts application 378, a voice dial application 379, an email application 380, a calendar application 381, a media player application 382, an album application 383, a clock application 384, a health care application (for example, measure exercise quantity or blood sugar), or environment information (for example, atmospheric pressure, humidity, or temperature information).

According to an embodiment of the present disclosure, the applications 370 may include an application (hereinafter, referred to as an "information exchange application" for convenience of description) supporting information exchange between the electronic device (for example, the electronic device 101) and an external electronic device (for example, the first external electronic device 102 or the second external electronic device 104). The information exchange application may include, for example, a notification relay application for transferring specific information to an external electronic device or a device management application for managing an external electronic device.

For example, the notification relay application may include a function of transferring, to the external electronic device (for example, the first external electronic device 102 or the second external electronic device 104), notification information generated from other applications of the electronic device (for example, an SMS/MMS application, an e-mail application, a health management application, or an environmental information application). Further, the notification relay application may receive notification information from, for example, an external electronic device and provide the received notification information to a user.

For example, the device management application may manage (for example, install, delete, or update) at least one function of an external electronic device (for example, the first external electronic device 102 or the second external electronic device 104) communicating with the electronic device (for example, a function of turning on/off the external electronic device itself (or some components) or a function of adjusting luminance (or a resolution) of the display), applications operating in the external electronic device, or services provided by the external electronic device (for example, a call service and a message service).

According to an embodiment of the present disclosure, the applications 370 may include an application (for example, a health care application of a mobile medical device, and the like) designated according to an attribute of the external electronic device (for example, the first external electronic device 102 or the second external electronic device 104). According to an embodiment of the present disclosure, the applications 370 may include an application received from the external electronic device (for example, the server 106, or the first external electronic device 102 or the second external electronic device 104). According to an embodiment of the present disclosure, the applications 370 may include a preloaded application or a third party application which can be downloaded from the server. Names of the elements of the program module 310, according to the above-described embodiments of the present disclosure, may change depending on the type of OS.

According to various embodiments of the present disclosure, at least some of the program module 310 may be implemented in software, firmware, hardware, or a combination of two or more thereof. At least some of the program module 310 may be implemented (e.g., executed) by, for example, the processor (e.g., the processor 120). At least some of the program module 310 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented.

For example, the "module", according to embodiments of the present disclosure, may include at least one of an application-specific IC (ASIC) chip, a field-programmable gate array (FPGA), and a programmable-logic device for performing operations which has been known or are to be developed hereinafter.

According to various embodiments of the present disclosure, at least some of the devices (for example, modules or functions thereof) or the method (for example, operations) according to the present disclosure may be implemented by a command stored in a non-transitory computer-readable storage medium in a programming module form. The instruction, when executed by a processor (e.g., the processor 120), may cause the one or more processors to execute the function corresponding to the instruction. The non-transitory computer-readable storage medium may be, for example, the memory 130.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include a Read-Only Memory (ROM), a Random-Access Memory (RAM), Compact Disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

The programming module, according to embodiments of the present disclosure, may include one or more of the aforementioned components or may further include other additional components, or some of the aforementioned components may be omitted. Operations executed by a module, a programming module, or other component elements, according to various embodiments of the present disclosure, may be executed sequentially, in parallel, repeatedly, or in a heuristic manner. Further, some operations may be executed according to another order or may be omitted, or other operations may be added. Various embodiments of the present disclosure disclosed herein are provided merely to easily describe technical details of the present disclosure and to help the understanding of the present disclosure, and are not intended to limit the scope of the present disclosure. Accordingly, the scope of the present disclosure should be construed as including all modifications or various other embodiments based on the technical idea of the present disclosure.

Figure 4:
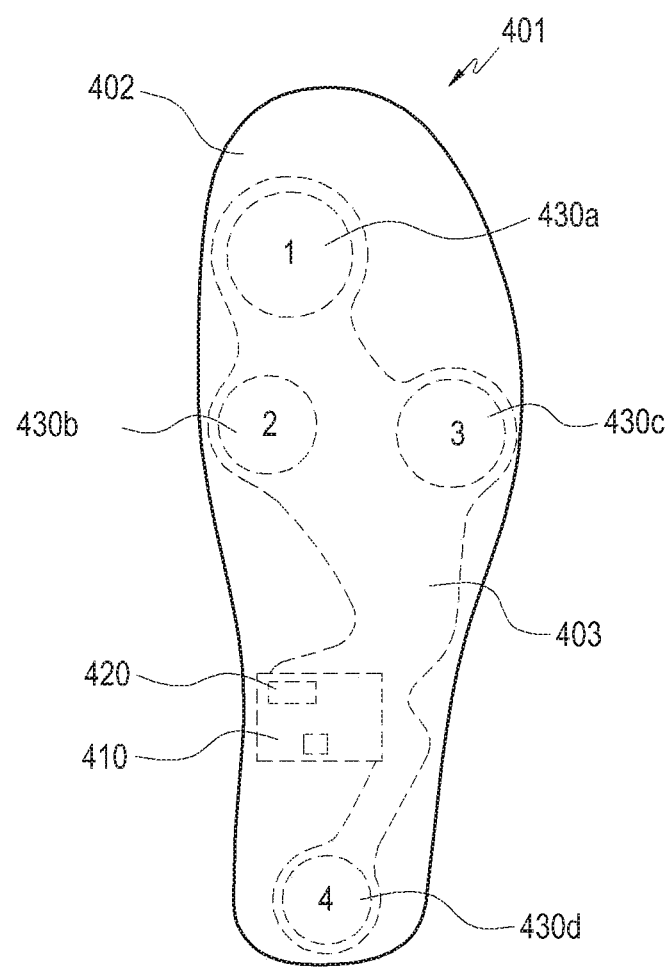
FIG. 4 illustrates a configuration of an electronic device according to various embodiments of the present disclosure.

FIG. 4 illustrates a configuration of an electronic device according to various embodiments of the present disclosure.

Referring to FIG. 4, an electronic device 401, according to various embodiments of the present disclosure, is an insole-type wearable electronic device, which may be located at a sole of the user, and may include a pad part 402, a flexible substrate 403, a controller 410, an inertia sensor 420, and pressure sensors 430a, 430b, 430c, and 430d. According to various embodiments of the present disclosure, the electronic device 401 may be implemented in the form of shoe or sock.

The pad part 402 may have the form of insole, which can be mounted to the shoe, and may include an upper pad and a lower pad. The flexible substrate 403, the controller 410, the inertia sensor 420, and the pressure sensors 430a, 430b, 430c, and 430d may be interposed between the upper pad and the lower pad.

The flexible substrate 403 may be installed inside the pad part 402 and may include a circuit for connecting the controller 410, the inertia sensor 420, and the pressure sensors 430a, 430b, 430c, and 430d, which are installed on the circuit.

The controller 410 may be mounted onto the flexible substrate 403, and control overall operations of the electronic device 401, the inertia sensor 420, and the pressure sensors 430a, 430b, 430c, and 430d.

The inertia sensor 420 may be mounted onto the flexible substrate 403, and may detect a change in an angle of a user's foot. The inertia sensor 420 may include a sensor module in which an acceleration sensor, a gyro sensor, and a geomagnetic sensor are combined, or at least one of the acceleration sensor, the gyro sensor, and the geomagnetic sensor. For example, the inertia sensor 420 may include a 3-axis acceleration sensor and a 3-axis gyro sensor and have six degrees of freedom. According to various embodiments of the present disclosure, the inertia sensor 420 may use a 2-axis sensor or three 1-axis sensors as necessary. The inertia sensor 420 is a sensor for basically measuring an 3-axis acceleration and a 3-axis angular speed, and a generally widely used strapdown inertial navigation system (SDINS) may calculate information on a position, a speed, and a posture of a three-dimensional moving object by using the 3-axis acceleration and the 3-axis angular speed. For example, the inertia sensor 420 may calculate a posture of the object by using an integral value of the angular speed and convert a moving object acceleration detected from the acceleration sensor through the integral value of the angular speed into an acceleration in an absolute coordinate system. The inertia sensor 420 may calculate the speed and the position by integrating the converted acceleration in the absolute coordinate system again.

The pressure sensors 430a, 430b, 430c, and 430d may be mounted onto the flexible substrate 403, and the multiple pressure sensors 430a, 430b, 430c, and 430d are needed to detect a change in pressure of the user's sole applied to the ground. The pressure sensors 430a, 430b, 430c, and 430d may be located at parts of the sole, that is, a toe part, a heel part, and an intermedia part of the sole. For example, among the pressure sensors 430a, 430b, 430c, and 430d, the first pressure sensor 430a may be located at the toe part, the second pressure sensor 430b and the third pressure sensor 430c may be located at the intermediate part of the sole, and the fourth pressure sensor 430d may be located at the heel part as illustrated in FIG. 4. According to various embodiments of the present disclosure, the number and form of the pressure sensors 430a, 430b, 430c, and 430d may vary for accurate measurement of the change in the pressure of the user's sole applied to the ground. The pressure sensors 430a, 430b, 430c, and 430d correspond to sensors for measuring changes in resistance and capacitance to calculate the pressure, and may determine a landing of the foot during the gait and detect a pressure distribution of each part of the sole at a moment of the landing.

Figure 5:
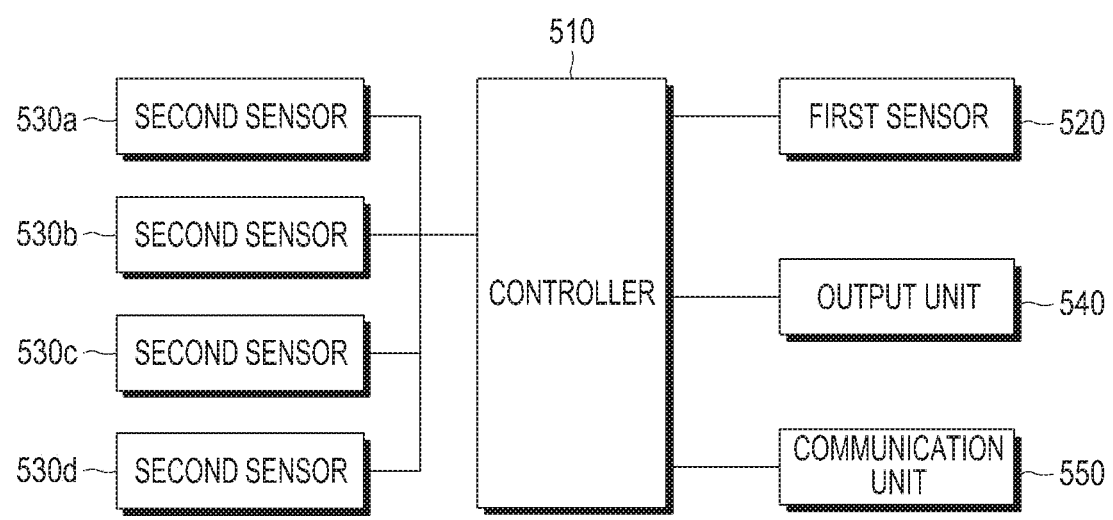
FIG. 5 is a block diagram illustrating an internal configuration of an electronic device according to various embodiments of the present disclosure.

FIG. 5 is a block diagram illustrating an internal configuration of an electronic device according to various embodiments of the present disclosure.

Referring to FIG. 5, the electronic device, according to various embodiments of the present disclosure, may include a controller 510, a first sensor 520, second sensors 530a, 530b, 530c, and 530d, an output unit 540, and a communication unit 550. The electronic device may include all or some of the electronic device 201 illustrated in FIG. 2. In an implementation of the actual application, two or more of the elements of the electronic device may be combined into one element or one of the elements of the electronic device may be subdivided into two or more elements as necessary.

The first sensor 520 may be an inertia sensor module, which may detect a change in an angle of the user's foot, and may include a 3-axis acceleration sensor and a 3-axis gyro sensor and have 6 degrees of freedom. The first sensor 520 may calculate information on a position, a speed, and a posture of a three-dimensional moving object by using a 3-axis acceleration and a 3-axis angular speed. For example, the inertia sensor may calculate the posture of the object by using an integral value of the angular speed and convert a moving object acceleration detected from the acceleration sensor through the integral value of the angular speed into an acceleration in an absolute coordinate system. The inertia sensor may calculate the speed and the location by integrating the converted acceleration in the absolute coordinate system again. According to various embodiments of the present disclosure, the first sensor 520 may use a 2-axis sensor or three 1-axis sensors as necessary. Further, the first sensor 520 may be configured through a combination of the acceleration sensor and the gyro sensor into one module or a separation of the acceleration sensor and the gyro sensor.

In addition, the first sensor 520 may further include a geomagnetic sensor to function as an electronic compass that may detect Earth's magnetism and mark an azimuth, and may measure an absolute direction of the toe regardless of a direction in which the user's feet move. According to various embodiments of the present disclosure, the first sensor 520 may be configured through a combination of the acceleration sensor, the gyro sensor, and the geomagnetic sensor into one module or a separation of the acceleration sensor, the gyro sensor, and the geomagnetic sensor.

The second sensors 530a, 530b, 530c, and 530d may correspond to pressure sensors that may detect the change in the pressure of the user's sole applied to the ground, and may measure a change in resistance and capacitance and calculate the pressure so as to determine a landing of the feet during the gait and detect a pressure distribute of each part of the sole at a moment of the landing. The number of second sensors 530a, 530b, 530c, and 530d may be plural to be located at respective parts of the user's sole, that is, a toe part, a heel part, and an intermediate part of the sole. For example, among the second sensors 530a, 530b, 530c, and 530d, the first sensor 530a of the second sensors may be located at the toe part, the second sensor 530b of the second sensors may be located at one side of the intermediate part of the sole, the third sensor 530c of the second sensors may be located at the other side of the intermediate part of the sole, and the fourth second sensor 530d may be located at the heel part. According to various embodiments of the present disclosure, the number and form of the second sensors 530a, 530b, 530c, and 530d may vary for accurate measurement of the change in the pressure of the user's sole applied to the ground.

According to various embodiments of the present disclosure, in addition to the first sensor 520 and the second sensors 530a, 530b, 530c, and 530d, various sensors that may detect user's body information (for example, a user's blood pressure, blood flow, heart rate, body temperature, respiration rate, heart and lung sound, electromyogram, ECG, and the like) may be further included. The various sensors may include at least one of a heart rate variability (HRV) sensor, a heart rate monitor (HRM) sensor, an EMG sensor, an EEG sensor, an ECG sensor, an IR sensor, and an E-nose sensor. Further, it is preferable that the first sensor 520, the second sensors 530a, 530b, 530c, and 530d, and the various sensors are located around the user's feet, but the present disclosure is not limited thereto, and embodiments of the present disclosure may further include an additional sensor module located at another part (for example, user's wrist, shoulder, chest, head, and the like), which is not the part around the user's feet.

The controller 510 may control the overall operations of the electronic device and control the operations of other elements (for example, the first sensor 520, the second sensors 530a, 530b, 530c, and 530d, the output unit 540, and the communication unit 550). The controller 510 may provide a signal or instruction required to control the operations of the elements included in the electronic device, provide data generated when the electronic device is driven, or receive information required to drive the electronic device.

The controller 510, according to various embodiments of the present disclosure, may be configured to control collection of sensor values detected through at least one of the first sensor 520 and the second sensors 530a, 530b, 530c, and 530d, control determination of the user's gait posture by using the detected sensor value, and control output of at least one of information on the user's gait posture, information on muscle fatigue of the user according to the gait, information on another joint fatigue of the user according to the gait, and information on a recommended exercise for the user through the output unit 540 based on the determined user's gait posture.

The controller 510 may determine the user's gait posture according to a detection order of the sensor values detected by the plurality of sensors. Further, the controller 510 may determine the user's gait posture according to sizes of the sensor values detected by the plurality of sensors. The controller 510 may determine the user's gait posture according to the detection or and the sizes of the sensor values detected by the plurality of sensors. The controller 510 may determine whether the user is in at least one of waking, running, and stopped states by using the sensor values detected by the plurality of sensors, and determine the user's gait posture according to the determined state.

The controller 510 may determine a user's gait period by using the detected sensor values, calculate a gait posture determination factor including at least one of a change in a pressure distribution of the user's feet according to the determined user's gait period, a change in an angle of the user's feet, a change in the center of gravity (COG) of the user, a change in a pressure of the user's feet when the user lands, and a change in an acceleration of the user's feet during exercise, and determine the user's gait posture based on the calculated gait posture determination factor. Further, the controller 510 may compare the calculated gait posture determination factor with a certain gait posture determination reference and determine the user's gait posture based on a type of the user's gait posture and a score of a level of normality or abnormality of the user's gait posture according to a result of the comparison.

According to various embodiments of the present disclosure, the controller 510 may determine the user's gait posture according to the detection order of the sensor values detected by the plurality of sensors. For example, the controller 510 may determine the user's gait posture according to the detection order of the pressure sensor values detected by the second sensors 530a, 530b, 530c, and 530d. For example, the controller 510 may determine an order of the change in the pressure distribution of the user's feet according to the landing by using the detection order of the pressure sensor values detected by the second sensors 530a, 530b, 530c, and 530d and determine the user's gait posture according to the determined order. Further, the controller 510 may determine the order and size of the change in the pressure distribution of the user's feet according to the landing by using the detection order and size of the pressure sensor values detected by the second sensors 530a, 530b, 530c, and 530d and determine the user's gait posture according to the determined order and size. For example, the controller 510 may determine whether the user executes a gait based on the change in the pressure distribution of the sole and the size according to the user's gait and determine the user's gait period. Further, the controller 510 may determine whether the user's gait corresponds to the normal gait or the abnormal gait based on the change in the pressure distribution of the sold according to the user's gait. The determination on whether the user's gait posture corresponds to the normal gait or the abnormal gait may be made based on a comparison between the pressure distribution change of the sole according to the user's gait with a certain reference pressure distribution change which may be generated when the user's gait corresponds to the normal gait. For example, when the pressure distribution change of the sole according to the user's gait corresponds to the reference pressure distribution change, the controller 510 may determine that the user's gait posture corresponds to the normal gait. When the pressure distribution change of the sole according to the user's gait is different from the reference pressure distribution change, the controller 510 may determine that the user's gait posture corresponds to the abnormal gait.

According to various embodiments of the present disclosure, the controller 510 may determine the user's gait posture according to the detection size of the sensor values detected by the plurality of sensors. For example, the controller 510 may determine the user's gait posture according to the detection size of an inertia sensor value detected by the first sensor 520. For example, the controller 510 may determine a change in an angle of the user's feet by using the detection size of the inertia sensor value detected by the first sensor 520 and determine the user's gait posture according to the detected change. Further, the controller 510 may determine an order and size of the change in the angle of the user's feet by using the detection order and size of the inertia sensor value detected by the first sensor 520 and determine the user's gait posture according to the detected order and size. For example, the controller 510 may determine various forms of gait posture according to the change in the angle of the feet according to the user's gait. It may be determined whether the user's gait posture corresponds to a normal gait, an out-toeing gait, an in-toeing gait, or an in-toeing or out-toeing gait of one leg by comparing the angle change of the user's feet according to the gait with reference to angle changes determined for at least one of a change in an angle of the feet which may be generated in the normal gait, a change in an angle of the feet which may be generated in the in-toeing gait, and a change in an angle of the feet which may be generated in the in-toeing or out-toeing gait of one leg. For example, it may be determined that the user's gait posture corresponds to the normal gait posture when the angle change of the user's feet according to the gait corresponds to the reference angle change according to the normal gait, it may be determined that the user's gait posture corresponds to the out-toeing gait posture when the angle change of the user's feet according to the gait corresponds to the reference angle change according to the out-toeing gait, it may be determined that the user's gait posture corresponds to the in-toeing gait posture when the angle change of the user's feet according to the gait corresponds to the reference angle change according to the in-toeing gait, and it may be determined that the user's gait posture corresponds to the in-toeing or out-toeing gait posture of one leg when the angle change of the user's feet according to the gait corresponds to the reference angle change according to the in-toeing or out-toeing gait of one leg. At this time, the reference angle change may be defined as an angle between the two feet.

According to various embodiments of the present disclosure, the controller 510 may determine the user's gait posture according to the detection size of the sensor values detected by the plurality of sensors. For example, the controller 510 may determine the user's gait posture according to the detection order of the pressure sensor values detected by the second sensors 530*a*, 530*b*, 530*c*, and 530*d* and the detection size of the inertia sensor value detected by the first sensor 520. Further, the controller 510 may determine the user's gait posture according to at least one of the detection order and size of the pressure sensor values detected by the second sensors 530*a*, 530*b*, 530*c*, and 530*d* and at least one of the detection order and size of the inertia sensor value detected by the first sensor 520. For example, the controller 510 may determine the user's gait period according to the detection order of the pressure sensor values detected by the second sensors 530*a*, 530*b*, 530*c*, and 530*d* and determine the user's gait posture by applying the detection size of the inertia sensor value detected by the first sensor 520. The user's gait posture may be more accurately determined based on a more detailed division of the user's gait into a time point when the feet is landed and a time point when the feet exercises.

According to various embodiments of the present disclosure, the controller 510 may determine the user's gait posture according to the detection order and size of the sensor values detected by the plurality of sensors. For example, the controller 510 may determine whether the user executes a gait according to the detection order and size of the pressure sensor values detected by the second sensors 530*a*, 530*b*, 530*c*, and 530*d*. Further, the controller 510 may determine a user's stopped posture according to the detection size of the pressure sensor values detected by the second sensors 530*a*, 530*b*, 530*c*, and 530*d*. For example, the controller 510 may determine the COG of the user by using the detection size of the pressure sensor values detected by the second sensors 530*a*, 530*b*, 530*c*, and 530*d* and determine the user's stopped posture according to the determined COG. The user's stopped posture may be determined according to the pressure distribution size of both feet when the user is in the stopped state. For example, it may be determined whether the user's stopped posture corresponds to a standing state, a sitting state, a standing state with leaning on one foot, or a sitting state with crossed legs by identifying the COG according to the pressure distribution size of both feet when the user is the stopped posture. The controller 510 may determine that the user's posture corresponds to the normally standing posture when the COG is located at an approximate center part in the user's stopped state, determine that the user's posture corresponds to the posture with leaning on one foot when the COG leans to one side of the approximate center part in the user's stopped state and the pressure distribution size of both feet corresponds to user's weight, and determine that the user's posture corresponds to the posture with crossed legs when the COG leans to one side of the approximate center part in the user's stopped state and the pressure distribution size of both feet is smaller than the user's weight.

According to various embodiments of the present disclosure, the controller 510 may determine whether the user's posture corresponds to at least one state of the walking, running, and stopped postures by using the sensor values detected by the plurality of sensors. For example, the controller 510 may identify a sensor value change pattern from at least one or a combination of the inertia sensor value detected by the first sensor 520 and the pressure sensor values detected by the second sensors 530*a*, 530*b*, 530*c*, and 530*d*, and determine which one of the waking, running, and stopped postures is the user's posture according to the identified sensor value change pattern. Since movements of the user's two feet have different forms in the walking, running, and stopped postures and accordingly the detected change patterns of the pressure sensor values and inertia sensor value are different, it may be determined which one of the waking, running, and stopped postures is the user's posture according to the change pattern. Further, the controller 510 may determine the user's gait posture according to the determined state. For example, when the determined state is the walking state, the controller 510 may compare the walking state with a gait posture determination reference determined for the walking state, and determine whether the user's walking is normal or abnormal according to a result of the comparison. When the user's walking state is abnormal, the controller 510 may determine gait postures of the user's walking, such as an out-toeing gait, an in-toeing gait, and an in-toeing or out-toeing gait of one leg. Further, when the determined state is the running state, the controller 510 may compare the running state with a gait posture determination reference determined for the running state, and determine whether the user's running is normal or abnormal according to a result of the comparison. When the user's running state is abnormal, the controller 510 may determine gait postures of the user's running, such as an out-toeing gait, an in-toeing gait, an in-toeing or out-toeing gait of one leg, and a tempo balance of both foot. In addition, when the determined state is the stopped state, the controller 510 may compare the stopped state with a stopped posture determination reference determined for the stopped state, and determine whether the user's stopped state corresponds to a sitting state or a standing state and whether such a posture is normal or abnormal based on a result of the comparison. When the posture is abnormal, the controller 510 may determine user's stopped posture, such as a posture with leaning on one foot and a posture with crossed legs.

According to various embodiments of the present disclosure, the controller 510 may determine the user's gait period by using the sensor values detected by the plurality of sensors. For example, the controller 510 may identify a sensor value change pattern from at least one or a combination of the inertia sensor value detected by the first sensor 520 and the pressure sensor values detected by the second sensors 530a, 530b, 530c, and 530d, and determine the user's gait period according to the identified sensor value change pattern. Since movements of the user's two feet have different forms during walking or running and accordingly the detected change patterns of the pressure sensor values and the inertia sensor value are different, the gait period may be determined according to the change pattern by repetition of a stance phase and a swing phase of both feet according to the user's walking or running. Further, the controller 510 may calculate a gait posture determination factor including at least one of the pressure distribution change of the user's foot according to the determined user's gait period, the angle change of the user's foot, the change in the COG of the user, and the pressure change when the user's feet land, and the acceleration change of the user's foot during exercise. The landing and exercise of the foot may be divided according to the user gait period and the gait posture determination factor may be acquired by calculating the sensor values detected at time points corresponding to the divided actions. Further, the controller 510 may compare the calculated gait posture determination factor with a certain gait posture determination reference and determine the user's gait posture based on at least one of a type of the user's gait posture and a score of a level of normality or abnormality of the user's gait posture according to a result of the comparison.

According to various embodiments of the present disclosure, the controller 510 may determine the user's gait posture according to the detection order and size of the sensor values detected by the plurality of sensors and output at least one of information on the user's gait posture, information on the muscle fatigue of the user according to the gait, information on the joint fatigue of the user according to the gait, and information on the recommended exercise for the user according to the detection order and size of the sensor values detected by the plurality of sensors. For example, the controller 510 may be configured to control determination of the user's gait posture by using the detected sensor values, and control output of at least one of state notification information on the user's gait posture, avatar information generated by shaping the user's gait posture, and guide information according to the user's gait posture through the output unit 540 in real time as information on the user's gait posture based on the determined user's gait posture. For example, the controller 510 may be configured to control output of the state notification information according to the user's gait posture through the output unit 540 in the form of sound or light. At this time, the output unit 540 may include a speaker for outputting a sound or an LED for radiating a light. Further, the controller 510 may be configured to control transmission of the information on the user's gait posture to an external electronic device using short-range communication through the communication unit 550 and output the information on the user's gait posture through the external electronic device. At this time, the external electronic device corresponds to an electronic device, which can perform short-range communication and may have a display unit and a speaker, and may include a smart phone, a tablet PC, a mobile phone, and a notebook computer. Further, the electronic device corresponds to a wearable electronic device and may include a glasses type, a head-mounted display (HMD) type, an earphone type, a necklace type, a shoe type, a waist belt type, an ankle band type, and a band type. In this case, the information on the user's gait posture may be an avatar generated by shaping the user's gait posture and may output the avatar as an image or a dynamic image. Further, the controller 510 may output the information on the user's gait posture in real time. In addition, the controller 510 may output the guide information to instruct the user to correct an improper gait posture while the user recognizes a state of the user's gait posture in real time. The guide information may output, for example, a certain sound source according to the user's gait posture. For example, when the user's gait posture corresponds to running, the controller 510 may output a sound source of a constant beat or a constant metronome rhythm while the user maintains the normal running having a regular tempo of steps of right and left feet and, during the abnormal running in which the tempo of the steps of the right and left feet is not regular, output a sound source in which the beat or metronome rhythm is changed to allow the user to immediately become aware. Further, in another example, when the user reproduces a separate sound source, the guide information may change the reproduced sound source according to the user's gait posture and output the changed sound source. For example, when the user's gait state corresponds to running, the controller 510 may output the reproduced original sound source while the user maintains the normal running having the regular tempo of the steps of the right and left feet. During the abnormal running in which the tempo of the steps of the right and left feet is not regular, the controller 510 may add noise to the reproduced sound source to allow the user to immediately become aware or change a speed of the sound source to be faster or slower and output the changed sound source. Further, the controller 510 may accumulate and store the information on the user's gait posture and provide the information in the form in which the accumulated information can be collectively determined according to a user's request.

According to various embodiments of the present disclosure, the controller 510 may determine the user's gait posture by using the detected sensor value and output information on the accumulated fatigue of the user based on the determined user's gait posture. For example, the controller 510 may determine the user's gait period according to the detection order and size of the pressure sensor values detected by the second sensors 530*a*, 530*b*, 530*c*, and 530*d*, calculate an impulse according to the gait by using the size of the pressure sensor value detected when the feet land according to the determined gait period, and calculate an exercise quantity according to the gait by using the size of the inertia sensor value detected when the feet land according to the determined gait period. The fatigue according to the gait may be determined according to the impulse and the exercise quantity according to the gait.

According to various embodiments of the present disclosure, the controller 510 may determine the user's gait posture by using the detected sensor value and output information on the recommended exercise for the user based on the determined user's gait posture. For example, when it is required to correct the posture according to the determined user's gait posture, the controller 510 may recommend an exercise suitable for the correction of the posture. Further, the controller 510 may recommend an exercise suitable for recovery of the fatigue according to the determined user's gait posture. The controller 510 may determine information on the accumulated fatigue according to the user's gait based on the determined user's gait posture and recommend an exercise suitable for the recovery of the determined accumulated fatigue. The controller 510 may provide an execution guide of the exercise selected by the user along with the information on the recommended exercise of the user. The controller 510 may output the information on the recommended exercise of the user, output a recommended exercise guide according to the recommended exercise selected by the user, determine a user's exercise state according to the recommended exercise guide, compare the determined user's exercise state with a certain reference exercise state, and output corresponding corrected exercise information. At this time, the recommended exercise guide may be associated with the COG of the user. For example, the recommended exercise guide may provide a reference guide of the COG preset for the proper COG according to the recommended exercise and provide exercise correction information to make the COG of the user correspond to the guide of the COG.

According to various embodiments of the present disclosure, the controller 510 may determine the user's gait posture by using the detected sensor value, generate human body modeling information according to a user's motion based on the determined user's gait posture, and output the generated human body modeling information. In this case, the controller 510 may collect an additional sensor value detected using an additional sensor located at another part, which is not the part around the user's sole and apply the additional sensor value to the user's gait posture so as to generate human body modeling information according to the a user's motion.

The controller 510, according to various embodiments of the present disclosure, may be configured to control collection of the sensor value detected using at least one of the first sensor 520 and the second sensors 530*a*, 530*b*, 530*c*, and 530*d* and control transmission of the detected sensor value to an external electronic device using short range communication through the communication unit 550. In this case, the controller 510 may serve as a sensor hub for controlling overall operations of the plurality of sensors, and may be configured to control collection of sensor values detected using the plurality of sensors and control transmission of the collected sensor values or data, which can be obtained through a simple calculation of the collected sensor values to the external electronic device using short range communication through the communication unit 550. The external electronic device may be configured to control determination of the user's gait posture by using the received sensor values and control output of at least one of information on the user's gait posture, information on the muscle fatigue of the user according to the gait, information on the joint fatigue of the user according to the gait, and information on the recommended exercise of the user based on the determined user's gait posture.

The output unit 540 may include a speaker or an LED, which may be implemented in an insole type wearable electronic device, which may be mounted to a shoe. According to various embodiments of the present disclosure, the output unit 540 may not be included in the electronic device and an output unit of the external electronic device having a communication connection with the device, may be used.

The communication unit 550 may establish a communication session with the external electronic device to perform data communication. For example, the communication unit 550 may communicate with the external electronic device through short range communication. Further, the communication unit 550 may support wireless communication including short range communication and may include at least one of, for example, Wi-Fi, BT, NFC, a GPS, and cellular communication (for example, LTE, LTE-A, CDMA, WCDMA, UMTS, WiBro, or GSM). In addition, the communication unit 550 may support wired communication including at least one of a USB, an HDMI, RS-232, and a POTS.

Figure 6:
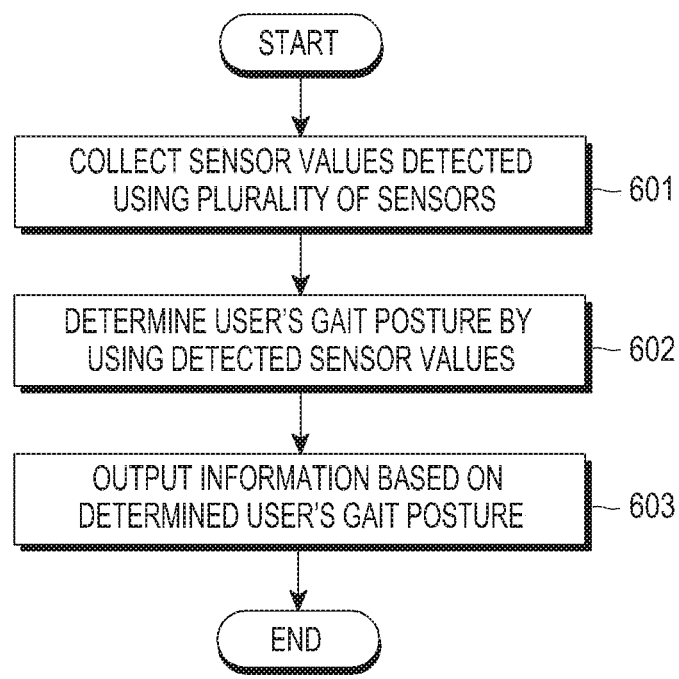
FIG. 6 is a flowchart illustrating a method of providing information based on a gait posture according to various embodiments of the present disclosure.

FIG. 6 is a flowchart illustrating a method of providing information based on a gait posture according to various embodiments of the present disclosure.

Referring to FIG. 6, in operation 601, the electronic device may collect sensor values detected using a plurality of sensors. The plurality of sensors may include a plurality of pressure sensors and an inertia sensor located within a pad part in the form of an insole of a shoe, and the inertia sensor may include at least one of an acceleration sensor, a gyro sensor, and a geomagnetic sensor. Further, the inertia sensor may detect a change in an angle of the user's foot, and may be configured by a sensor module generated by combining the acceleration sensor, the gyro sensor, and the geomagnetic sensor or include at least one of the acceleration sensor, the gyro sensor, and the geomagnetic sensor. For example, the inertia sensor may include a 3-axis acceleration sensor and a 3-axis gyro sensor and have six degrees of freedom. According to various embodiments of the present disclosure, the inertia sensor may use a 2-axis sensor or three 1-axis sensors as necessary. Further, the plurality of pressure sensors may detect a change in a pressure of the user's sole applied to the ground, and may be located at parts of the sole, that is, a toe part, a heel part, and an intermediate part of the sole.

In operation 602, the electronic device may determine a user's gait posture by using the detected sensor values. The user's gait posture may be determined according to a detection order of the sensor values detected by the plurality of sensors or seize of the detected sensor values. Further, through the inertia sensor among the plurality of sensors, the angle of the user's feet may be determined and the user's gait posture may be determined using the angle. The electronic device may determine the user's gait posture by using at least one of a change in a pressure distribution of the user's feet determined from the detected sensor values, the change in the angle of the user's feet, a change in the COG of the user, a gait period of the user according to the gait, a change in a pressure of the feet at a moment of the landing according to the user's gait period, and a change in an acceleration of the feet in an exercise according to the user's gait period.

In operation 603, the electronic device may output information based on the determined user's gait posture. The information may be output as at least one of visual, auditory, and audiovisual information through a speaker or an LED embedded in the electronic device. Further, the electronic device may transmit the information to an external electronic device by using short range communication and the information may be output through the external electronic device having received the information. The information may be at least one of information on the user's gait posture, information on the muscle fatigue of the user according to the gait, information on the joint fatigue of the user according to the gait, and information on the recommended exercise for the user, and the information on the recommended exercise for the user may include at least one of recommended exercise information for a recovery of the fatigue of the user according to the gait, recommended exercise information for a correction of the user's gait posture, and an execution guide of the recommended exercise.

Figure 7:
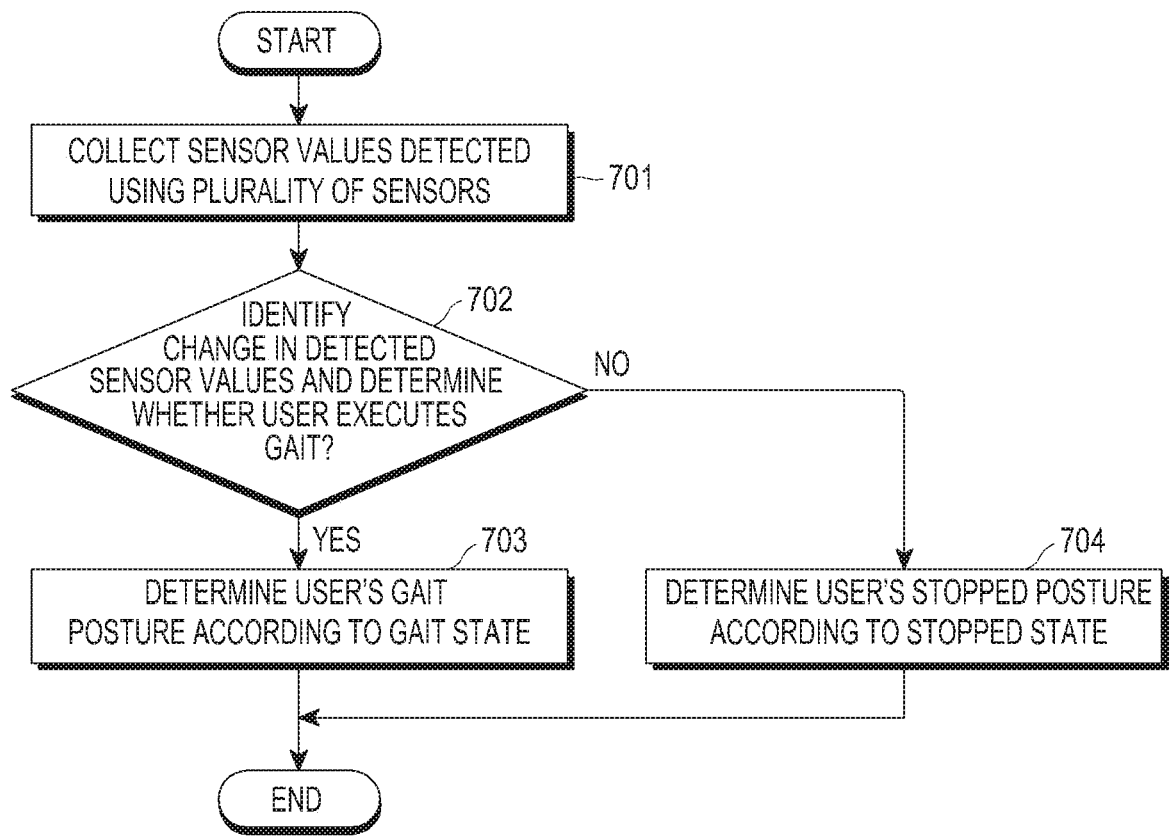
FIG. 7 is a flowchart illustrating a method of determining a gait posture according to various embodiments of the present disclosure.
Figures 8A, 8B, 8C:
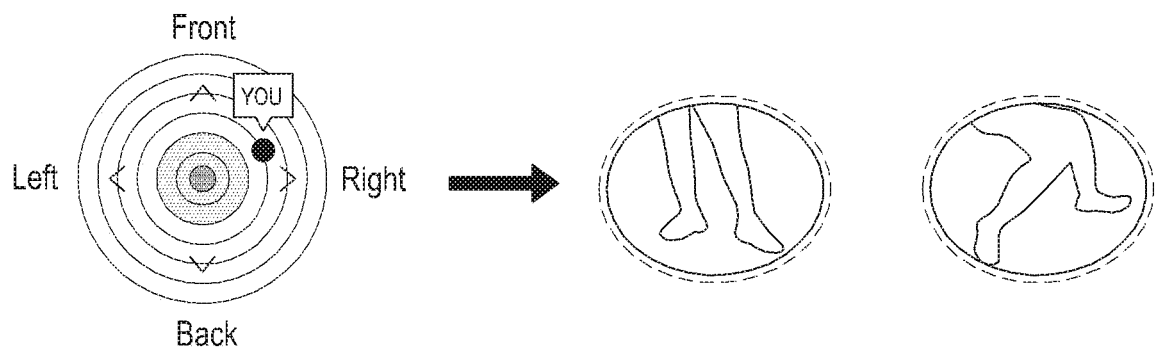
FIGS. 8A to 8C illustrate a method of determining a stopped posture according to various embodiments of the present disclosure.

FIG. 7 is a flowchart illustrating a method of determining a gait posture according to various embodiments of the present disclosure, and FIGS. 8A to 8C illustrate a method of determining a stopped posture according to various embodiments of the present disclosure.

Hereinafter, the method of determining the gait posture according to various embodiments of the present disclosure will be described below in detail with reference to FIGS. 7 to 8C.

Referring to FIG. 7, in operation 701, the electronic device may collect sensor values detected using a plurality of sensors.

In operation 702, the electronic device may determine whether the user executes a gait by identifying changes in the detected sensor values. The electronic device may determine whether the user's gait corresponds to one of walking, running, and stopped postures by using the detected sensor values and determine whether the user walks according to whether the user executes a gait according to whether the user is in the walking or running state or in the stopped state. A sensor value change pattern may be identified from at least one or a combination of the inertia sensor value detected by the inertia sensor and the sensor values detected by the plurality of pressure sensors and it may be determined whether the user executes a gait according to whether the user is in the walking or running state or in the stopped state based on the identified sensor value change pattern. For example, whether the user executes a gait may be determined according to a change and size of the pressure distribution, which is changed by a contact between the user's feet and the ground, that is, whether the user executes a gait may be determined according to a frequency of the pressure distribution change.

When it is determined that the user executes a gait, the electronic device may compare the gait state with a gait posture determination reference determined for the gait state and determine whether the user's gait is normal or abnormal according to a result of the comparison. When the user's gait is abnormal, the electronic device may determine gait postures, such as an out-toeing gait, an in-toeing gait, and an in-toeing or out-toeing gait of one leg in operation 703. When the gait state corresponds to running, the electronic device may determine the gait posture including a tempo balance of both foot.

When the electronic device determines that the user is not in the gait state, the electronic device may compare the stopped state with a stopped posture determination reference determined for the stopped state, and determine whether the user's stopped state corresponds to a sitting state or a standing state and whether such a posture is normal or abnormal based on a result of the comparison. When the posture is abnormal, the electronic device may determine user's stopped postures, such as a posture with leaning on one foot and a posture with crossing legs in operation 704. For example, the user's stopped posture according to the COG may be determined according to the size of the detected pressure sensor values. The electronic device may determine the COG of the user by using the size of the detected sensor values and determine the user's stopped posture according to the determined COG. When the user is in the stopped state, the user's stopped posture may be determined according to the size of pressure distribution on both feet. When the user has the stopped posture, the electronic device may identify a location of the COG according to the size of the pressure distribution on the two feet and determine whether the user's stopped posture corresponds to a standing state, a sitting state, a standing state with leaning on one foot, or a sitting state with crossed legs.

Referring to FIGS. 8A to 8C, the electronic device may provide location information on the COG in the user's stopped state. The electronic device may determine that the user's posture corresponds to a normal standing posture when the user is located approximately in a center part in the stopped state as illustrated in FIG. 8A, determine that the user's posture corresponds to a standing posture with leaning on one foot as illustrated in FIG. 8B when the COG leans toward one side from the approximately center part in the stopped state and the size of the pressure distribution on the two feet corresponds to the user's weight, and determine that the user's posture corresponds to a sitting posture with crossed legs as illustrated in FIG. 8C when the COG leans toward one side from the approximately center part in the stopped state and the size of the pressure distribution on the two feet is smaller than the user's weight.

Figure 9:
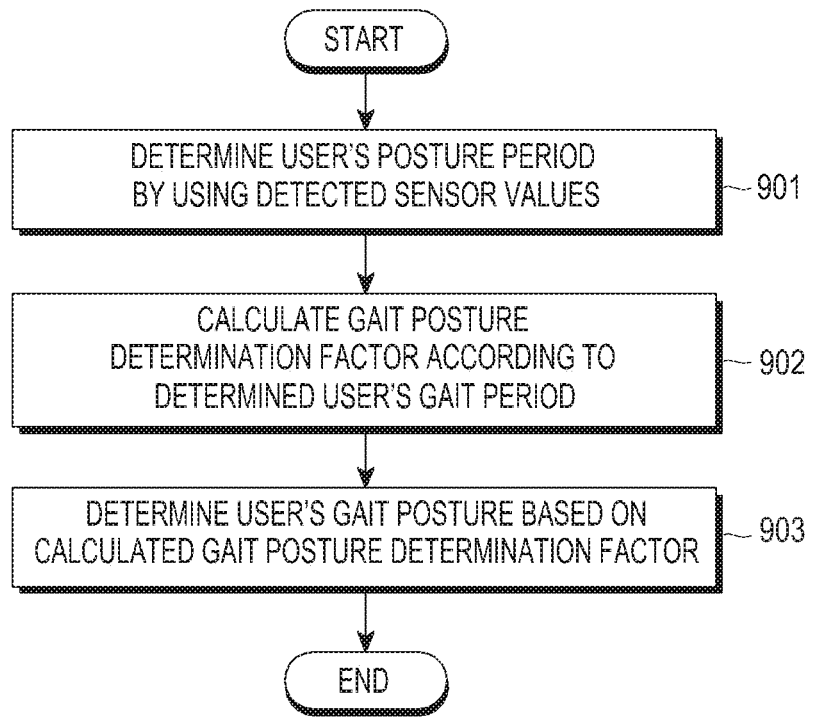
FIG. 9 is a flowchart illustrating a method of determining a gait posture according to various embodiments of the present disclosure.

FIG. 9 is a flowchart illustrating a method of determining a gait posture according to various embodiments of the present disclosure, and FIGS. 10A and 10B illustrate a method of determining a gait posture according to various embodiments of the present disclosure.

Hereinafter, the method of determining the gait posture according to an embodiment of the present disclosure will be described below in detail with reference to FIGS. 9 to 10B.

Referring to FIG. 9, in operation 901, the electronic device may determine a user's gait period by using detected sensor values. For example, the electronic device may identify a sensor value change pattern from at least one or a combination of the sensor value detected by the inertia sensor and the pressure sensor values detected by the pressure sensors and determine the user's gait period according to the identified sensor value change pattern. Since movements of the user's two feet have different forms during walking or running and accordingly the detected change patterns of the pressure sensor values and the inertia sensor value are different, the gait period may be determined according to the change pattern by repetition of a stance phase and a swing phase of the two feet according to the user's walking or running.

In operation 902, the electronic device may calculate a gait posture determination factor according to the determined user's gait period. For example, the electronic device may calculate a gait posture determination factor including at least one of a pressure distribution change of the user's foot according to the determined user's gait period, an angle change of the user's foot, a change in the COG of the user, and a pressure change of the user's foot at a moment of landing, and an acceleration change of the user's foot during exercise. The landing and exercise of the foot may be divided according to the user gait period and the gait posture determination factor may be acquired by calculating the sensor values detected at time points when the divided actions.

In operation 903, the electronic device may determine the user's gait posture based on the calculated gait posture determination factor. For example, the electronic device may compare the calculated gait posture determination factor with a certain gait posture determination reference and determine the user's gait posture based on at least one of a type of the user's gait posture and a score of a level of normality or abnormality of the user's gait posture according to a result of the comparison.

For example, the user's gait posture may be determined according to the change in the pressure distribution of the user's foot included in the gait posture determination factor which may be calculated based on the detection order and size of the pressure sensor values. The determination on whether the user's gait posture corresponds to the normal gait or the abnormal gait may be made based on a comparison between the pressure distribution change of the user's foot with a certain reference pressure distribution change of the foot which may be generated when the user's gait corresponds to the normal gait.

Referring to FIGS. 10A and 10B, when the pressure distribution of the user's foot is changed as illustrated in FIG. 10A(a), it may be determined that the user's gait posture corresponds to the normal gait. When the pressure distribution of the user's foot is changed as illustrated in FIG. 10A(b), it may be determined that the user's gait posture corresponds to the abnormal gait.

According to another example, the user's gait posture may be determined according to the angle change of the user's feet included in the gait posture determination factor which may be calculated based on the detection order and size of the pressure sensor values and the inertia sensor values. It may be determined whether the user's gait posture corresponds to a normal gait, an out-toeing gait, an in-toeing gait, or an in-toeing or out-toeing gait of one leg by comparing the angle change of the user's feet according to the gait with reference angle changes determined for at least one of a change in an angle of the feet which may be generated in the normal gait, a change in an angle of the feet which may be generated in the in-toeing gait, and a change in an angle of the feet which may be generated in the in-toeing or out-toeing gait of one leg. For example, as illustrated in FIG. 10B, it may be determined that the user's gait posture corresponds to the normal gait posture when an angle between the user's two feet is 7 to 15 degrees as illustrated in FIG. 10B(a), it may be determined that the user's gait posture corresponds to the out-toeing gait posture when an angle between the user's two feet is larger than or equal to 15 degrees as illustrated in FIG. 10B(b), it may be determined that the user's gait posture corresponds to the in-toeing gait posture when an angle between the user's two feet is 0 degrees as illustrated in FIG. 10B(c), and it may be determined that the user's gait posture corresponds to the in-toeing or out-toeing gait of one leg when one of the user's two feet is inward or outward as illustrated in FIG. 10B(d).

FIGS. 11A to 11C are views illustrating a method of determining a gait posture according to various embodiments of the present disclosure.

According to another example, the user's gait posture may be determined according to the change in the COG of the user and the angle change of the user's feet included in the gait posture determination factor which may be calculated according to the size of the pressure sensor values. Further, the certain gait posture determination reference may be defined in the form of a table including scores, and the user's gait posture may be determined through a comparison between the gait posture determination factor and the score table. For example, when the user is in a standing state included in the stopped state, the posture of the standing state of the user may be determined based on a score calculated through a method of linearly reducing a score according to a value (parameter r) indicating by how much X and Y coordinate values of the COG of the user escape from the center.

Referring to FIG. 11A, when the calculated score ranges from 50 to 100, the user's gait posture may be determined as normal. When the calculated score ranges from 0 to 49, the user's posture gait may be determined as abnormal. In this case, whether the user leans on a right leg or a left leg may be determined according to whether the COG leans toward the right foot or left foot.

When the user is in a sitting state included in the stopped state, the posture of the sitting state of the user may be determined based on a score calculated using a score according to a value (parameter r) indicating by how much the X and Y coordinate values of the COG of the user escape from the center and a score calculated through a method of inversely proportionally reducing a score according to a time (parameter r) during which crossed legs continues when the sitting state is a crossed leg state.

Referring to FIG. 11B, when the calculated score ranges from 30 to 0, the user's gait posture may be determined as abnormal sitting with crossed legs. In this case, whether crossing the legs is made by a right leg or a left leg may be determined according to whether the COG leans toward the right leg or left leg. When the calculated score ranges from 100 to 30, the user's posture gait may be determined as normal.

When the user is in a walking state included in the gait state, it may be determined whether the user's walking corresponds to a normal, in-toeing, or out-toeing gait according to data on an angle (parameter a) between the user's two feet, and the posture of the walking state of the user may be determined based on a score according to the angle (parameter r) and a score calculated using a score according to normality (parameter n) of the gait.

Referring to FIG. 11C, when the calculated score ranges from 50 to 0, the user's gait posture may be determined as abnormal and whether the user's gait is the out-toeing gait or the in-toeing gait may be determined according to the angle. When the calculated score ranges from 100 to 51, the user's posture gait may be determined as normal.

Figure 12:
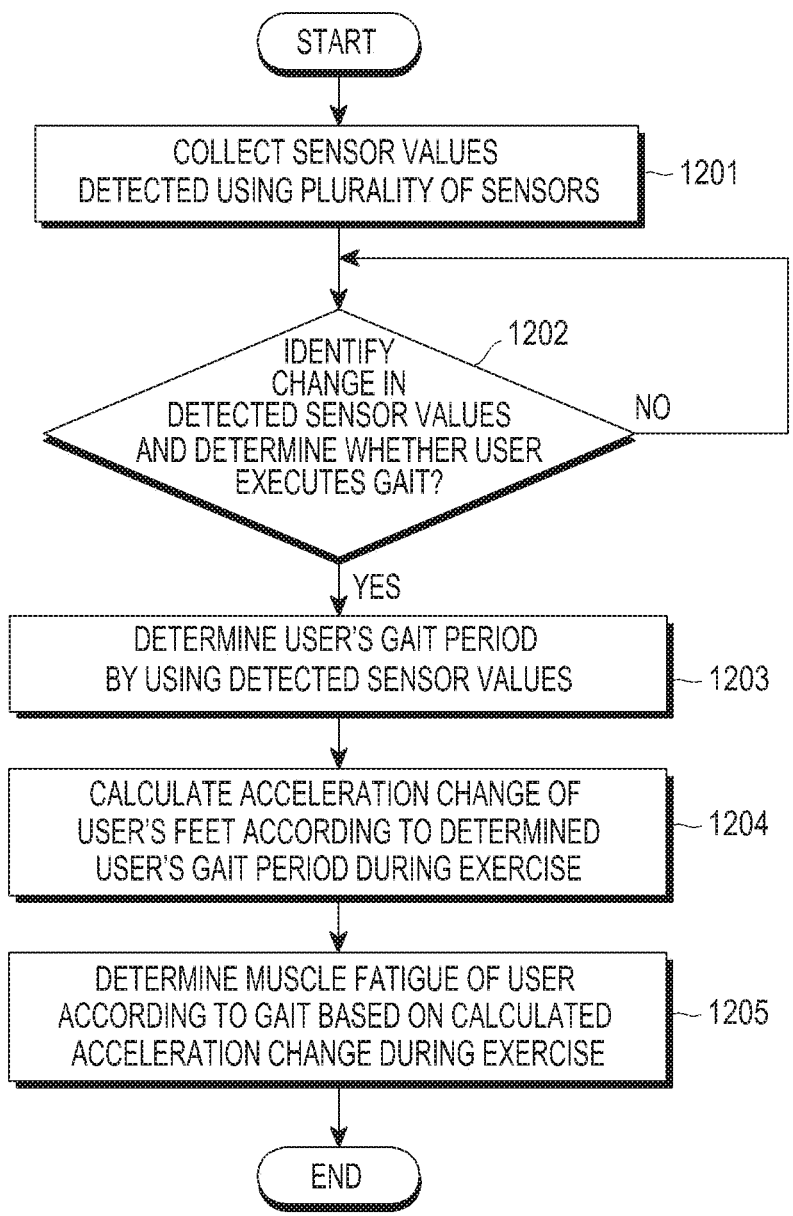
FIG. 12 is a flowchart illustrating a method of determining information based on a gait posture according to various embodiments of the present disclosure.
Figure 13:
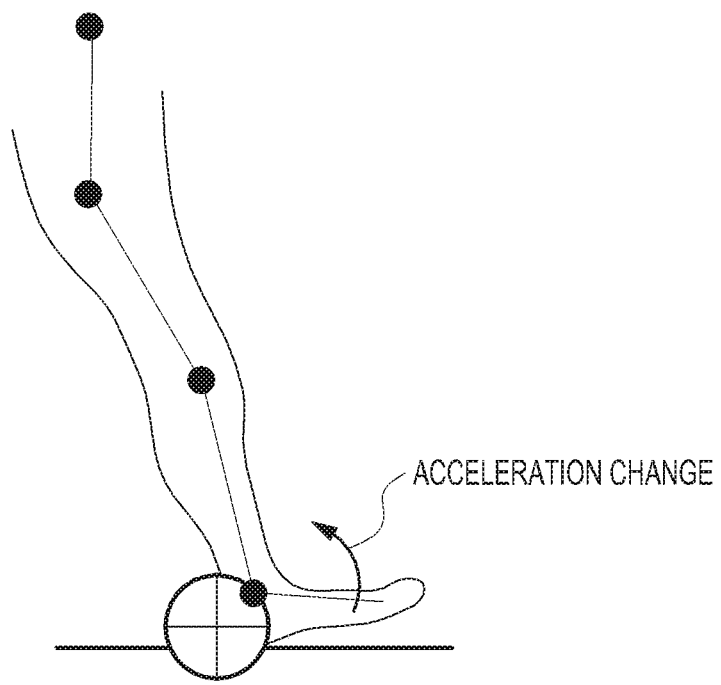
FIG. 13 illustrates a method of determining information on a gait posture according to various embodiments of the present disclosure.

FIG. 12 is a flowchart illustrating a method of determining information based on a gait posture according to various embodiments of the present disclosure, and FIG. 13 illustrates a method of determining information based on a gait posture according to various embodiments of the present disclosure.

Hereinafter, the method of determining the information based on the gait posture according to various embodiments of the present disclosure will be described below in detail with reference to FIGS. 12 and 13.

Referring to FIG. 12, in operation 1201, the electronic device may collect sensor values detected using a plurality of sensors.

In operation 1202, the electronic device may determine a user's gait posture by identifying changes in the detected sensor values. The electronic device may determine whether the user's gait corresponds to one of walking, running, and stopped postures by using the detected sensor values and determine the existence or non-existence of the gait according to whether the user is in the gait state, such as walking or running or in the stopped state. A sensor value change pattern may be identified from at least one or a combination of the inertia sensor value detected by the inertia sensor and the sensor values detected by the plurality of pressure sensors and it may be determined whether the user is in the gait state, such as walking or running or in the stopped state according to identified sensor value change pattern. For example, the existence or non-existence of the gait of the user may be determined according to a change and size of the pressure distribution, which is changed by a contact between the user's feet and the ground, and the existence or non-existence of the gait of the user may be determined according to a frequency of the pressure distribution change.

When it is determined that the user executes the gait, the electronic device may determine a user's gait period by using detected sensor values in operation 1203.

In operation 1204, the electronic device may calculate an acceleration change of the user's feet during an exercise according to the determined gait period.

Referring to FIG. 13, the electronic device may calculate an acceleration change when the user's foot leaves the ground and moves into the air according to the user's gait period, that is, when a top of the foot moves upwards during a swing.

In operation 1205, the electronic device may determine a user's muscle fatigue according to the calculated acceleration change of the feet. Forces of a shin muscle and a thigh muscle may be known through a calculation of a force (F=ma) according to the calculated acceleration change of the feet, and thus the muscle fatigue may be determined. For example, the electronic device may calculate a reduction amount of the calculated acceleration change during the exercise of the feet according to the user's gait and determine muscle fatigue information according to the calculated reduction amount of the acceleration change.

Figure 14:
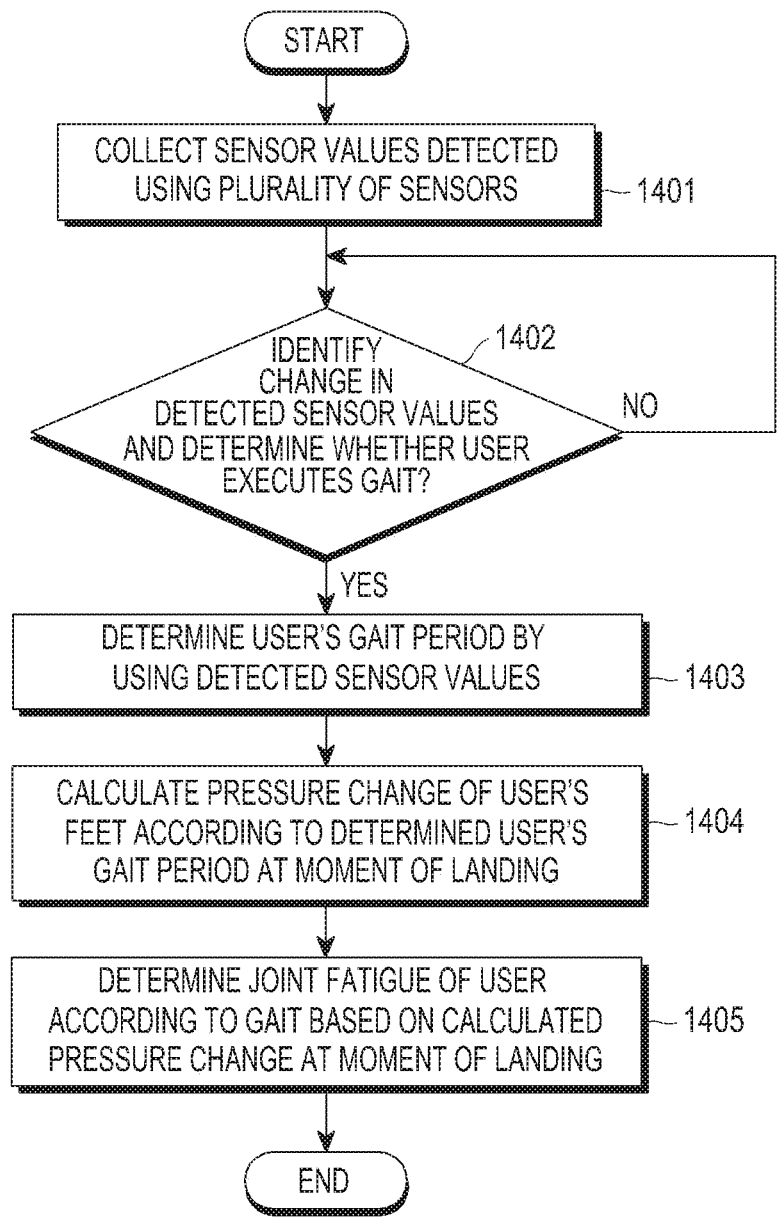
FIG. 14 is a flowchart illustrating a method of determining information based on a gait posture according to various embodiments of the present disclosure.
Figure 15:
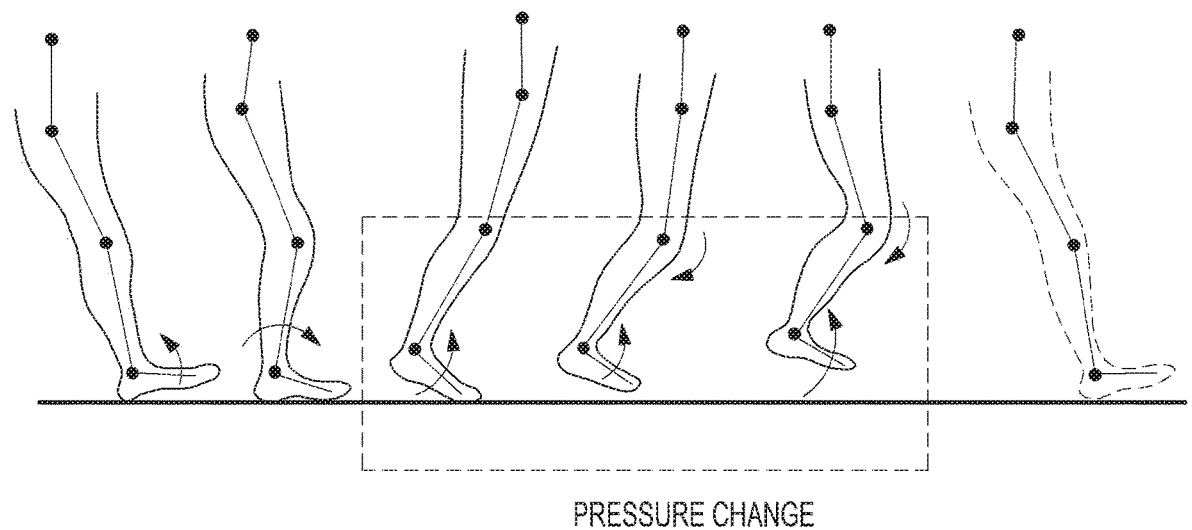
FIG. 15 illustrates a method of determining information on a gait posture according to various embodiments of the present disclosure.

FIG. 14 is a flowchart illustrating a method of determining information based on a gait posture according to various embodiments of the present disclosure, and FIG. 15 illustrates a method of determining information based on a gait posture according to various embodiments of the present disclosure.

Hereinafter, the method of determining the information based on the gait posture according to various embodiments of the present disclosure will be described below in detail with reference to FIGS. 14 and 15.

Referring to FIG. 14, in operation 1401, the electronic device may collect sensor values detected using a plurality of sensors.

In operation 1402, the electronic device may determine a user's gait posture by identifying changes in the detected sensor values.

When it is determined that the user executes the gait, the electronic device may determine a user's gait period by using detected sensor values in operation 1403.

In operation 1404, the electronic device may calculate a pressure change of the user's feet at a moment of the landing according to the determined gait period. For example, referring to FIG. 15, the electronic device may calculate a change in the pressure applied to the feet during a process in which the foot completely touches the ground and leave the ground according to the user's gait period.

In operation 1405, the electronic device may determine a user's joint fatigue according to the calculated pressure change of the feet. A force applied to each joint may be calculated by applying the calculated pressure change of the feet to preset dynamic human body modeling and determine a joint fatigue level according to the calculated force applied to each joint.

Figure 16:
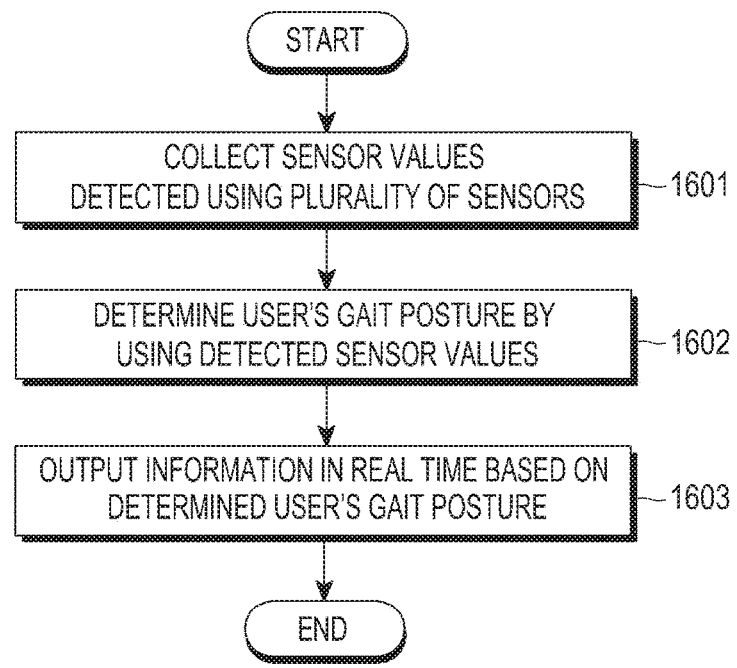
FIG. 16 is a flowchart illustrating a method of providing information based on a gait posture according to various embodiments of the present disclosure.

FIG. 16 is a flowchart illustrating a method of providing information based on a gait posture according to various embodiments of the present disclosure, and FIGS. 17A to 17E illustrate screens that provide information according to a gait posture according to various embodiments of the present disclosure.

The method of providing the information based on the gait posture according to an embodiment of the present disclosure will be described below in detail with reference to FIGS. 16 to 17E.

Referring to FIG. 16, in operation 1601, the electronic device may collect sensor values detected using a plurality of sensors.

In operation 1602, the electronic device may determine a user's gait posture by using the detected sensor values.

In operation 1603, the electronic device may output real time information based on the determined user's gait posture. The information may include at least one of state notification information on the user's gait posture, information on an avatar formalizing the user's gait posture, and guide information according to the user's gait posture. The electronic device may be an insole type wearable electronic device, which may be mounted onto a shoe, and may include a speaker or an LED. In this case, as the state notification information according to the user's gait posture, a notification sound or a light may be output in real time when the gait posture is abnormal in a user's gait process.

Further, the electronic device may establish a communication session with an external electronic device to transmit information on the user's gait posture to the external electronic device through short range communication or to transmit the detected sensor values to the external electronic device, and thus the external electronic device may perform processes 1602 and 1603 above. In this case, the state notification information may be configured to provide notification information on a user's particular gait posture and, accordingly, state notification information may be output.

Figure 17A:
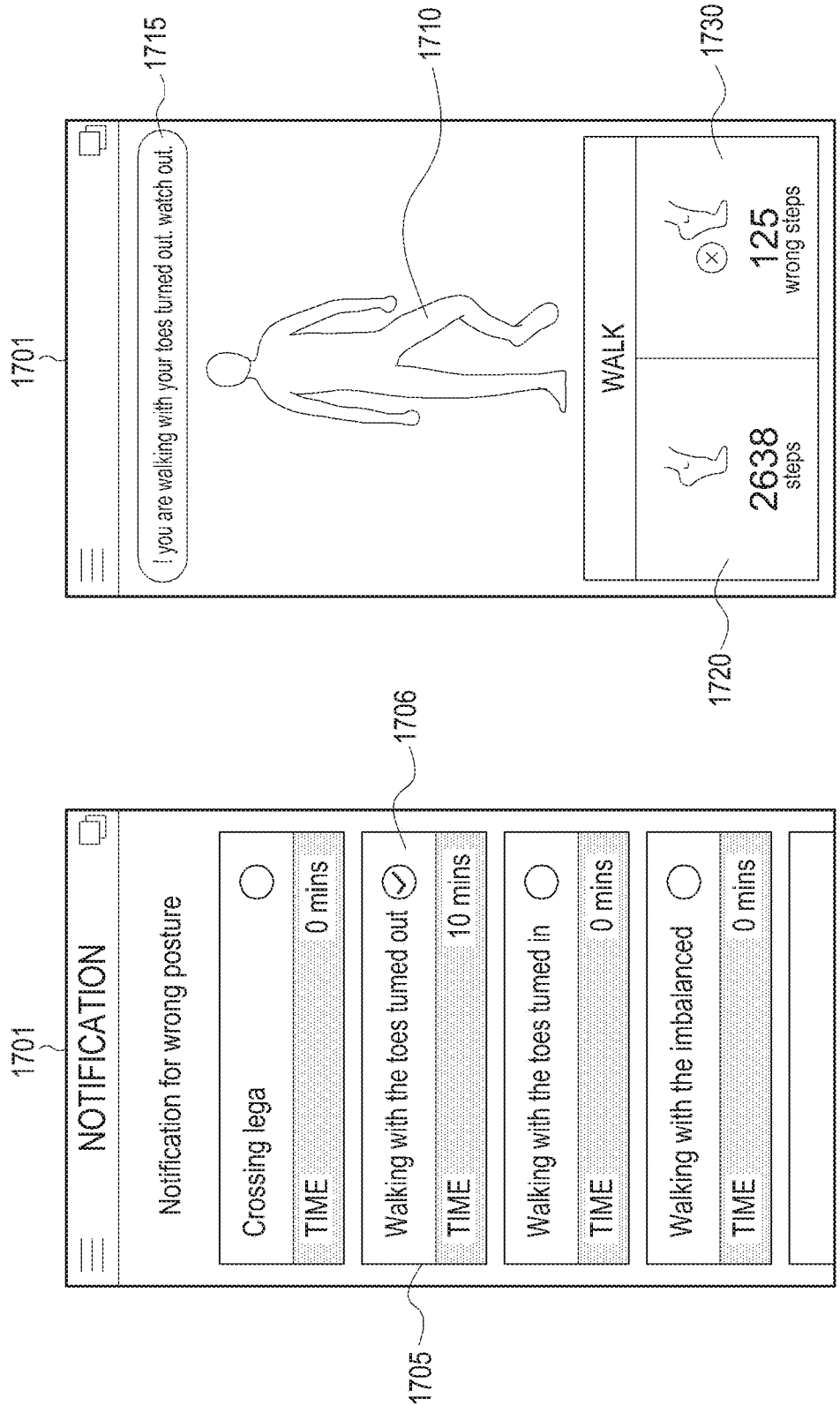

Referring to FIG. 17A, a screen 1701 for outputting state notification information may be provided. In FIG. 17A(a), an option list 1705 for configuring state notification information may be displayed and the state notification information may be provided according to an option 1706 selected from the option list by the user. For example, the option 1706 may be an option for providing notification information when the user walks with the toes turned out and the walking continues for 10 minutes or longer. When the option is satisfied, avatar information 1710 on the user's walking with the toes turned out may be displayed, the notification information may be displayed by text information 1715, and normal step information 1720 indicating a normal step generated in a process in which the user walks for a certain time as a numerical value and abnormal step information 1730 indicating an abnormal step through a numerical value may be displayed as illustrated in FIG. 17A(b). Further, as the avatar information according to the user's gait posture, an avatar generated by formalizing the user's gait posture may be output in the form of an image or a dynamic image in real time.

Figure 17B:
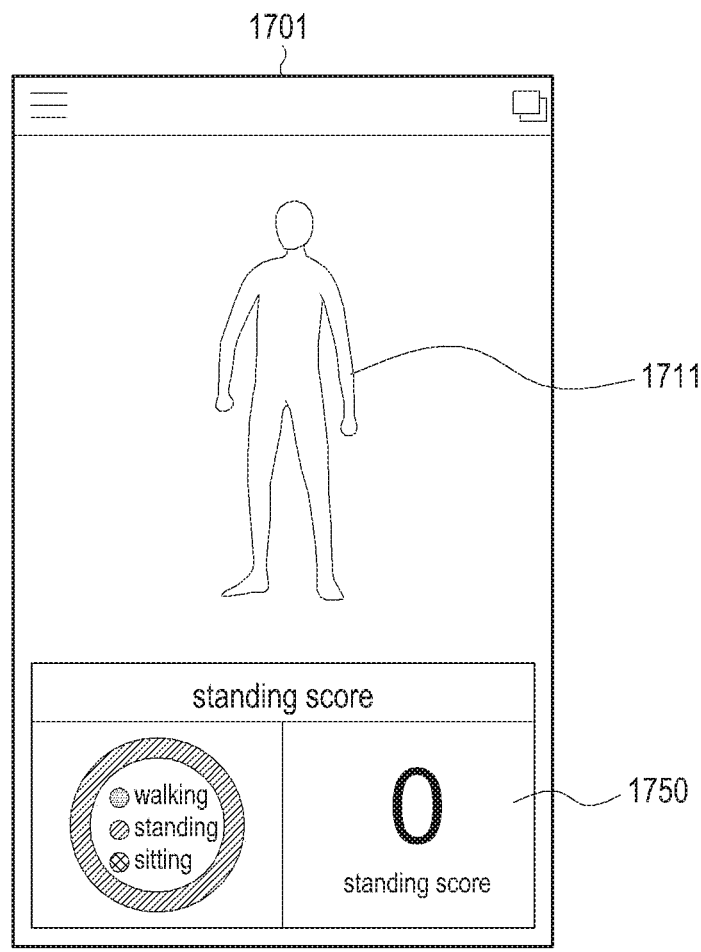

Referring to FIG. 17B, avatar information 1711 generated by shaping a user's standing posture may be displayed.

Referring to FIG. 17C, avatar information 1712a, 1712b, and 1712c formalizing a user's sitting posture may be displayed. At this time, according to the user's sitting posture, the avatar information may be classified into avatar information 1712a of a normal sitting posture, avatar information 1712b of a right leg-crossed posture in an abnormal sitting posture, and avatar information 1712c of a left leg-crossed posture in the abnormal sitting posture.

Referring to FIG. 17D, avatar information 1713a, 1713b, and 1713c generated by shaping a user's walking posture may be displayed. At this time, according to the user's walking posture, the avatar information may be classified into avatar information 1713a of a normal walking posture, avatar information 1713b of an out-toeing gait posture in an abnormal walking posture, and avatar information 1713c of an in-toeing gait posture in the abnormal walking posture. In addition, score information 1750 indicating a state of each posture by using a numerical value may be displayed.

Figure 17E:
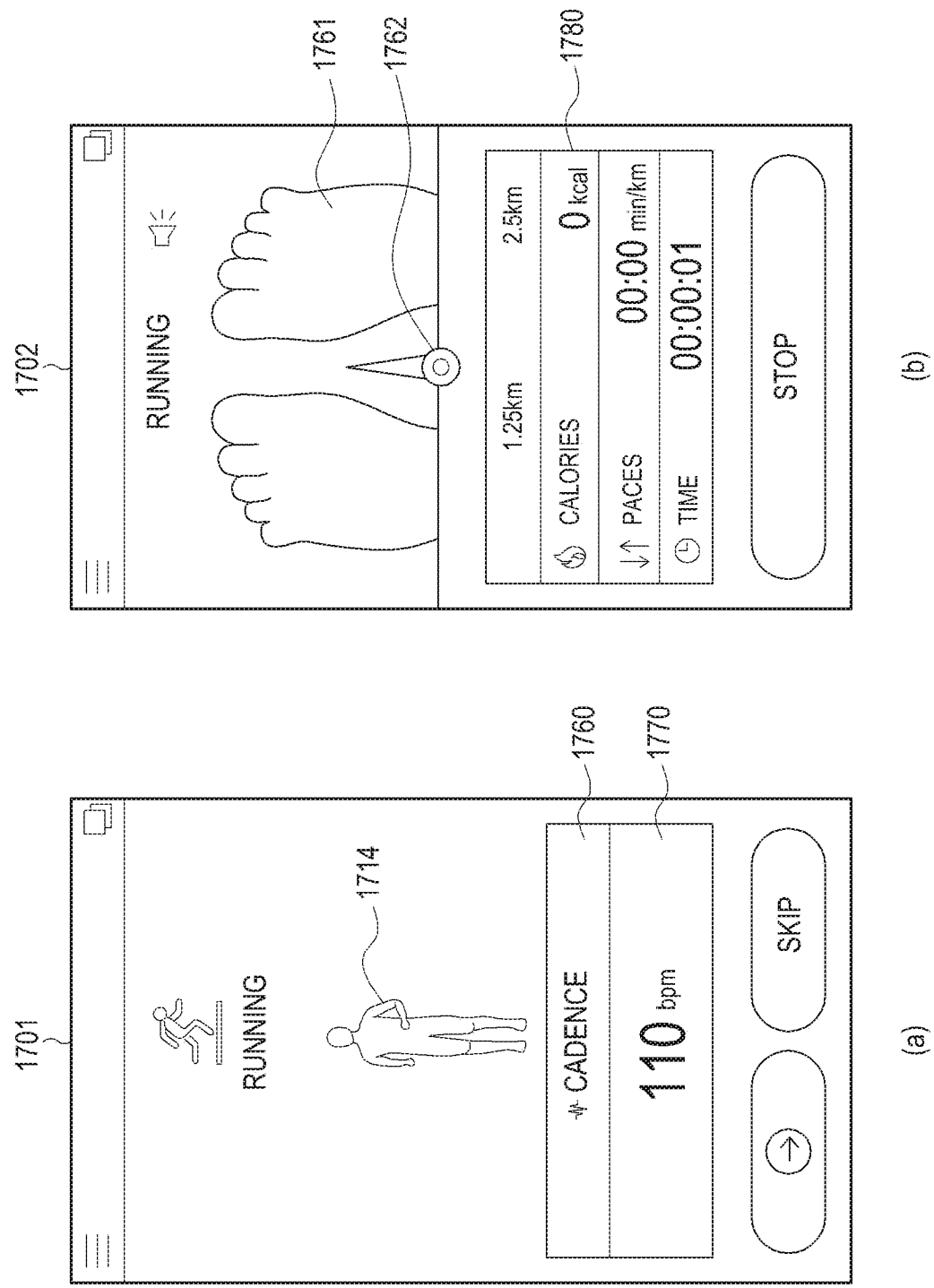

Referring to FIG. 17E, avatar information 1714 formalizing a user's running posture may be displayed in FIG. 17E(a). At this time, on a running posture information screen, a button 1760 for requesting detailed information on a running step tempo and information 1770 indicating the running step tempo as a simple numerical value may be displayed. When the user touches the button 1760, a guide information screen 1702 according to the running posture may be provided as illustrated in FIG. 17E(b). The guide screen 1702 may display information 1761 indicating a step of user's feet, information 1762 indicating whether the tempo leans toward a right foot or a left foot, and information 1780 indicating burnt calories, paces, and time according to the running.

In addition, the electronic device may output guide information to instruct the user to correct an improper gait posture while allowing the user to recognize the current gait posture in real time through the information on the user's gait posture. The guide information may output, for example, a certain sound source according to the user's gait posture. For example, when the user's gait posture corresponds to running, the electronic device may output a sound source of a constant beat or a constant metronome rhythm while the user maintains the normal running having a regular tempo of steps of right and left feet and, during the abnormal running in which the tempo of the steps of the right and left feet is not regular, output a sound source in which the beat or metronome rhythm is changed to allow the user immediately become aware. Further, in another example, when the user reproduces a separate sound source, the guide information may change the reproduced sound source according to the user's gait posture and output the changed sound source. For example, when the user's gait state corresponds to running, the controller 510 may output the reproduced original sound source while the user maintains the normal running having the regular tempo of the steps of the right and left foot. During the abnormal running in which the tempo of the steps of the right and left foot is not regular, the controller 510 may add noise to the reproduced sound source to allow the user to immediately become aware or change a speed of the sound source to be faster or slower and output the changed sound source.

Figure 18:
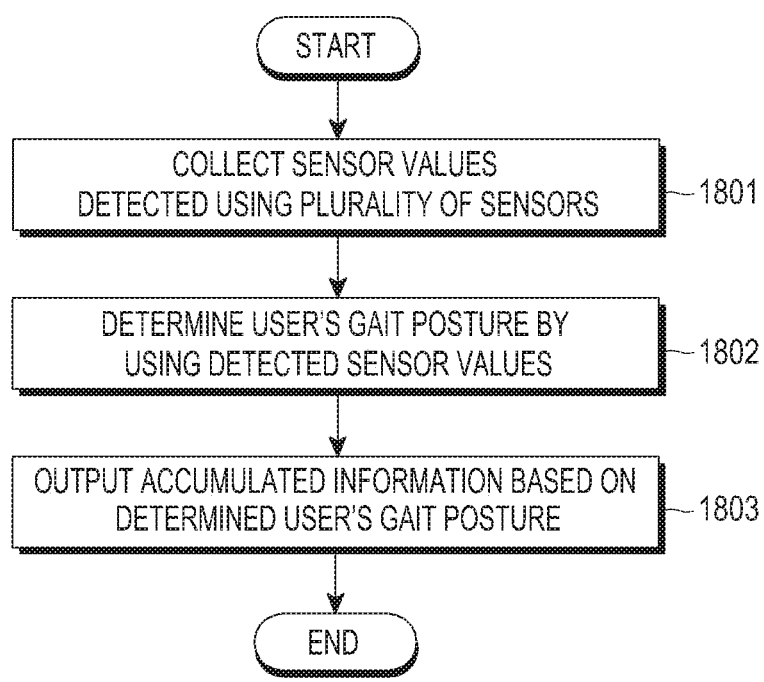
FIG. 18 is a flowchart illustrating a method of providing information based on a gait posture according to various embodiments of the present disclosure.

FIG. 18 is a flowchart illustrating a method of providing information based on a gait posture according to various embodiments of the present disclosure, and FIGS. 19A to 19D illustrate screens that provide information according to a gait posture according to various embodiments of the present disclosure.

The method of providing the information based on the gait posture according to an embodiment of the present disclosure will be described below in detail with reference to FIGS. 18 to 19D.

Referring to FIG. 18, in operation 1801, the electronic device may collect sensor values detected using a plurality of sensors.

In operation 1802, the electronic device may determine a user's gait posture by using the detected sensor values.

In operation 1803, the electronic device may output accumulated information based on the determined user's gait posture. The accumulated information may be generated by accumulating and storing the information on the user's gait posture for a certain time and the accumulated information may be provided in the form which may be collectively determined according to a user's request. Further, the accumulated information is information which may be acquired when the user's gait continues for a certain time and may include at least one of information on muscle fatigue of the user according to the gait and information on joint fatigue of the user according to the gait.

The electronic device may determine a user's gait period based on the determination on the user's gait posture performed in operation 1802, calculate an acceleration change of the user's feet according to the determined user's gait period during exercise, determine the muscle fatigue of the user according to the gait based on the calculated acceleration change of the feet during the exercise, and output the information on the muscle fatigue of the user according to the gait based on a result of the determination. For example, the electronic device may calculate an acceleration change when the user's foot leaves the ground and moves into the air, that is, when a top of the foot moves upwards in a swing, and determine the user's muscle fatigue according to the calculated acceleration change of the foot. Forces of a shin muscle and a thigh muscle may be known through a calculation of a force (F=ma) according to the calculated acceleration change of the feet, and thus the muscle fatigue may be determined. For example, the electronic device may calculate a reduction amount of the calculated acceleration change during the exercise of the feet according to the user's gait and determine a muscle fatigue level according to the calculated reduction amount of the acceleration change. The electronic device may output the information on the determined muscle fatigue.

The electronic device may determine a user's gait period based on the determination on the user's gait posture performed in operation 1802, calculate a pressure change of the user's feet according to the determined user's gait period at a moment of the landing, determine the joint fatigue of the user according to the gait based on the calculated pressure change of the feet at the moment of the landing, and output the information on the joint fatigue of the user according to the gait based on a result of the determination. For example, the electronic device may calculate the pressure change applied to the feet during a process in which the foot completely touches the ground and leaves the ground according to the user's gait period and determine the user's joint fatigue according to the calculated pressure change of the feet. A force applied to each joint may be calculated by applying the calculated pressure change of the feet to preset dynamic human body modeling and determine a joint fatigue level according to the calculated force applied to each joint. The electronic device may output information on the determined joint fatigue.

Further, the electronic device may establish a communication session with an external electronic device to transmit information on the user's gait posture to the external electronic device through short range communication or to transmit the detected sensor values to the external electronic device, and thus the external electronic device may perform processes 1802 and 1803 above.

Figure 19A:
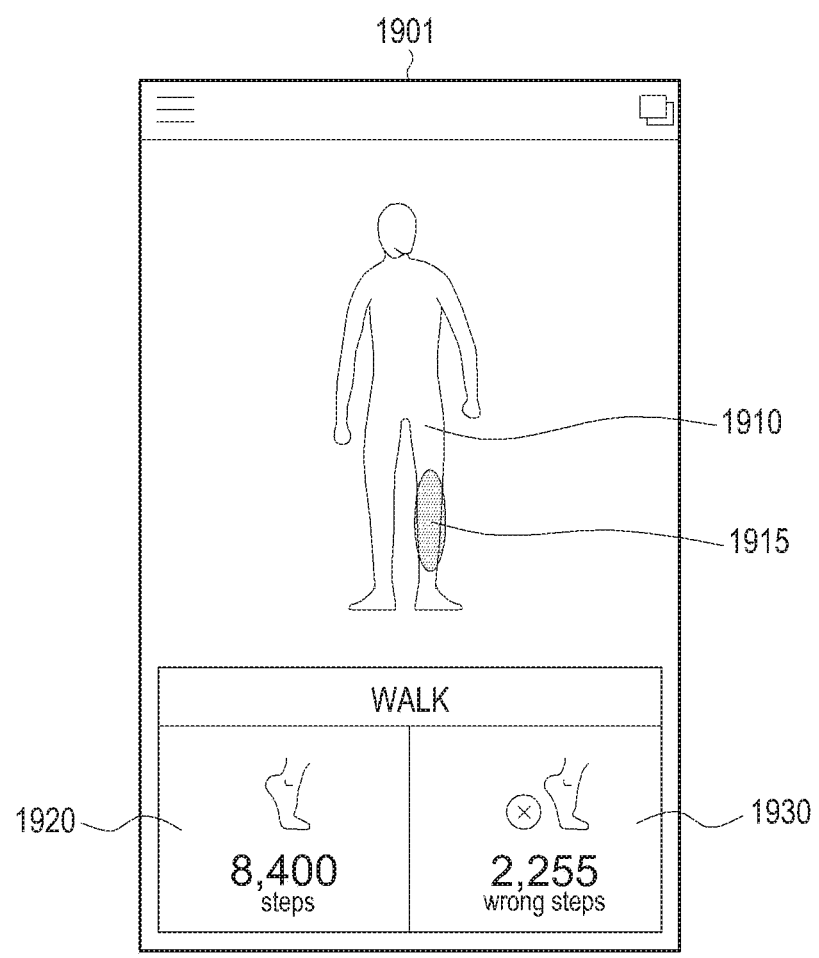
FIGS. 19A to 19D illustrate screens for providing information according to a gait posture according to various embodiments of the present disclosure.

Referring to FIG. 19A, a screen 1901 for outputting information on the muscle fatigue and the joint fatigue according to the gait may be provided. The output screen 1901 may display avatar information 1910 on the user, and accumulated fatigue information 1915 indicating a joint part or a muscle part of the user in which the fatigue is accumulated may be displayed on the avatar information 1910. Further, normal step information 1920 indicating normal steps, which are generated during a process in which the user executes a gait for a certain time, as a numerical value, and abnormal step information 1930 indicating abnormal steps as a numerical value. At this time, the accumulated fatigue information 1915 may be visually displayed in the joint part or the muscle part in which the fatigue is accumulated by using a number, a color, or a contour to make a difference according to a fatigue level, so that the user can intuitively recognize the fatigue level.

Figure 19B:
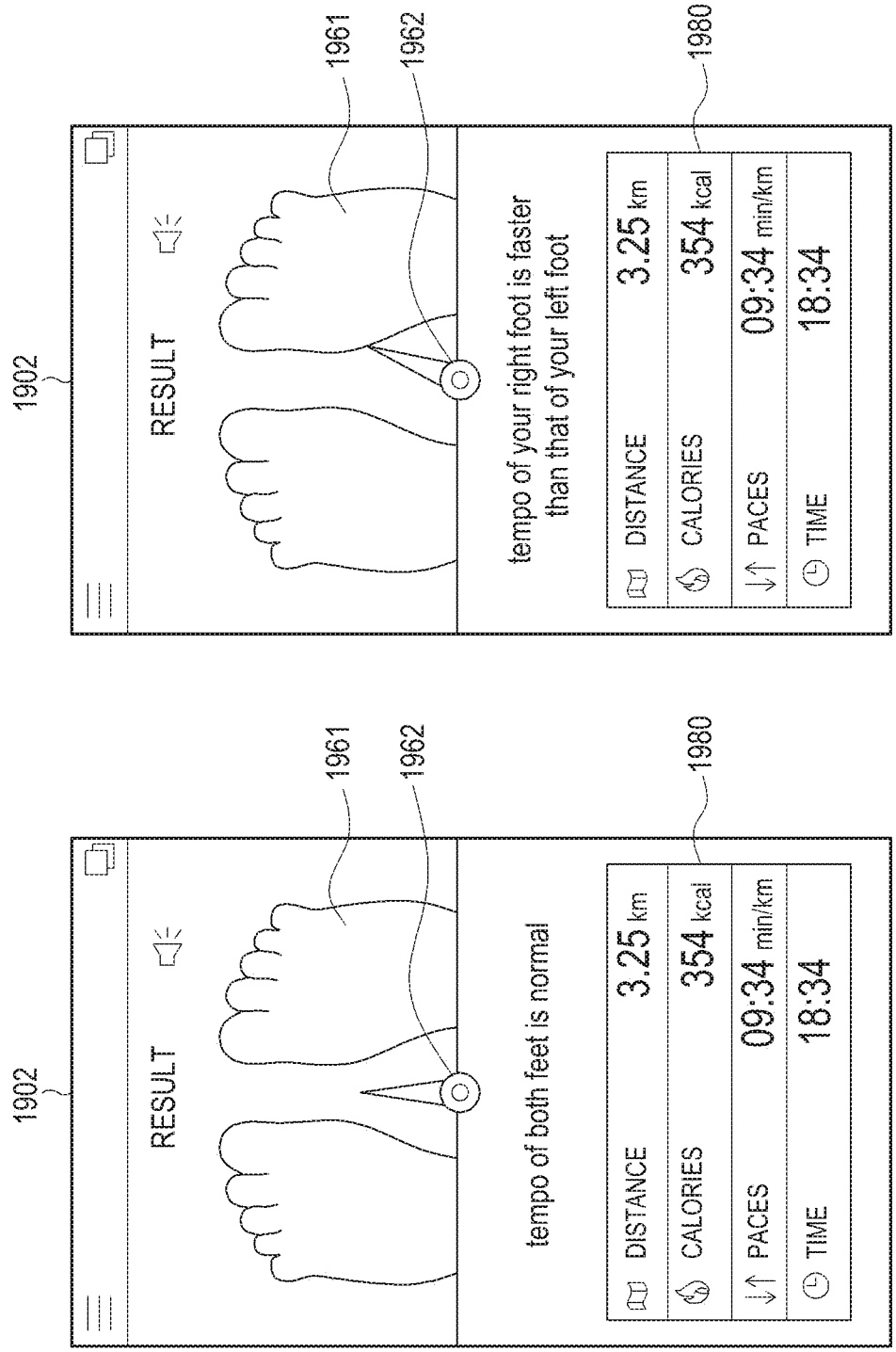

Referring to FIG. 19B, a screen 1902 for outputting aggregate result information from guide information according to the user's gait posture, which is accumulated for a certain time, may be provided. The output screen 1902 may display information 1961 indicating a step of user's feet, information 1962 indicating whether the tempo leans toward a right foot or a left foot, and information 1980 indicating a movement distance, burnt calories, paces, and time according to the running. For example, as illustrated in FIG. 19B(a), when the tempo of the user's two feet maintains a certain balance, the information 1962 indicating the step balance of the feet may point to the center between both feet, and text information "tempo of your feet is normal" may be displayed below the information 1962. Further, as illustrated in FIG. 19B(b), when the tempo of the user's two feet leans toward one side, the information 1962 indicating the step balance of the feet may point to one of the two feet, and text information "tempo of your right foot is faster than that of your left foot" may be displayed below the information 1962.

Figure 19C:
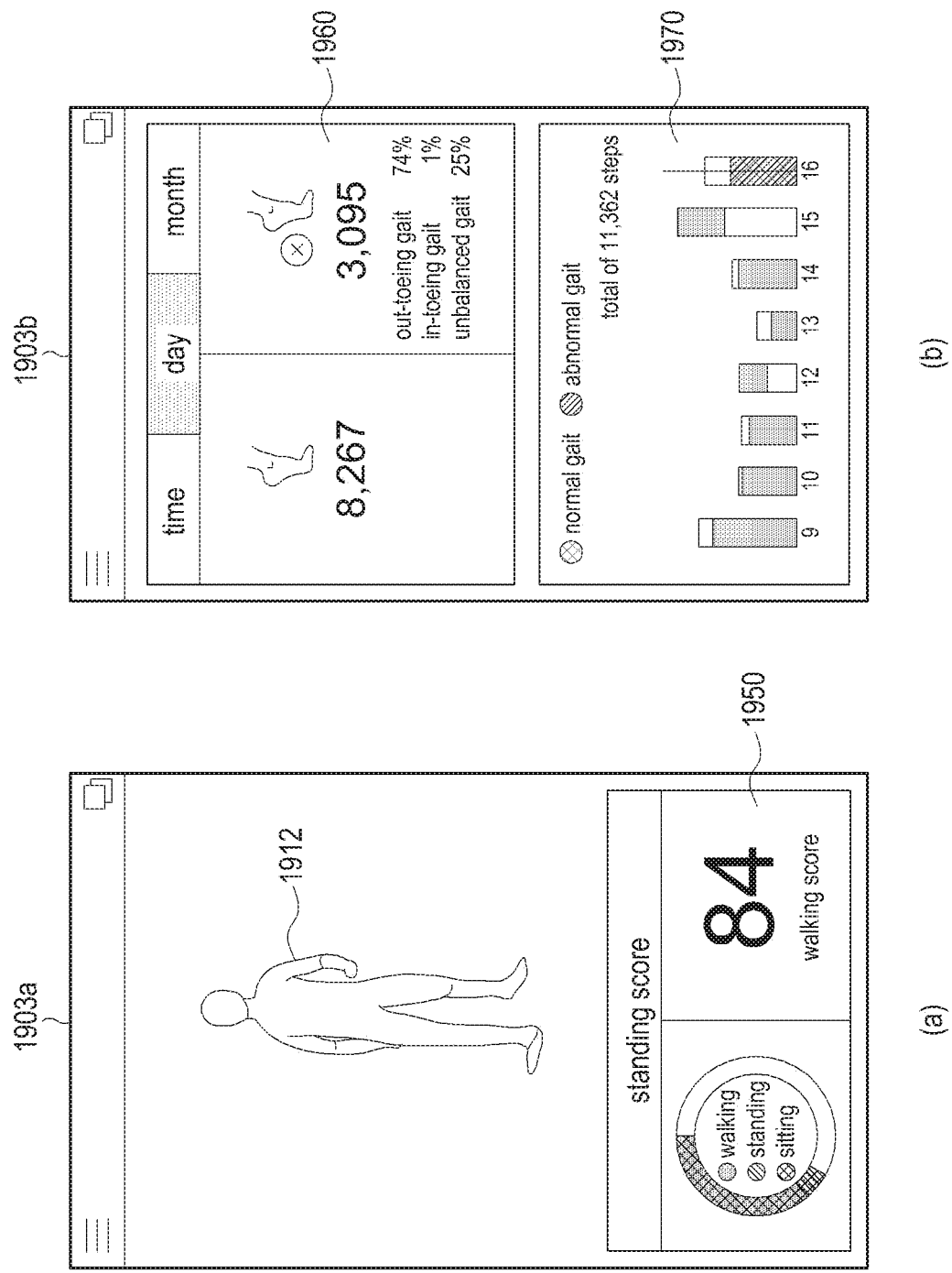
Figure 19D:
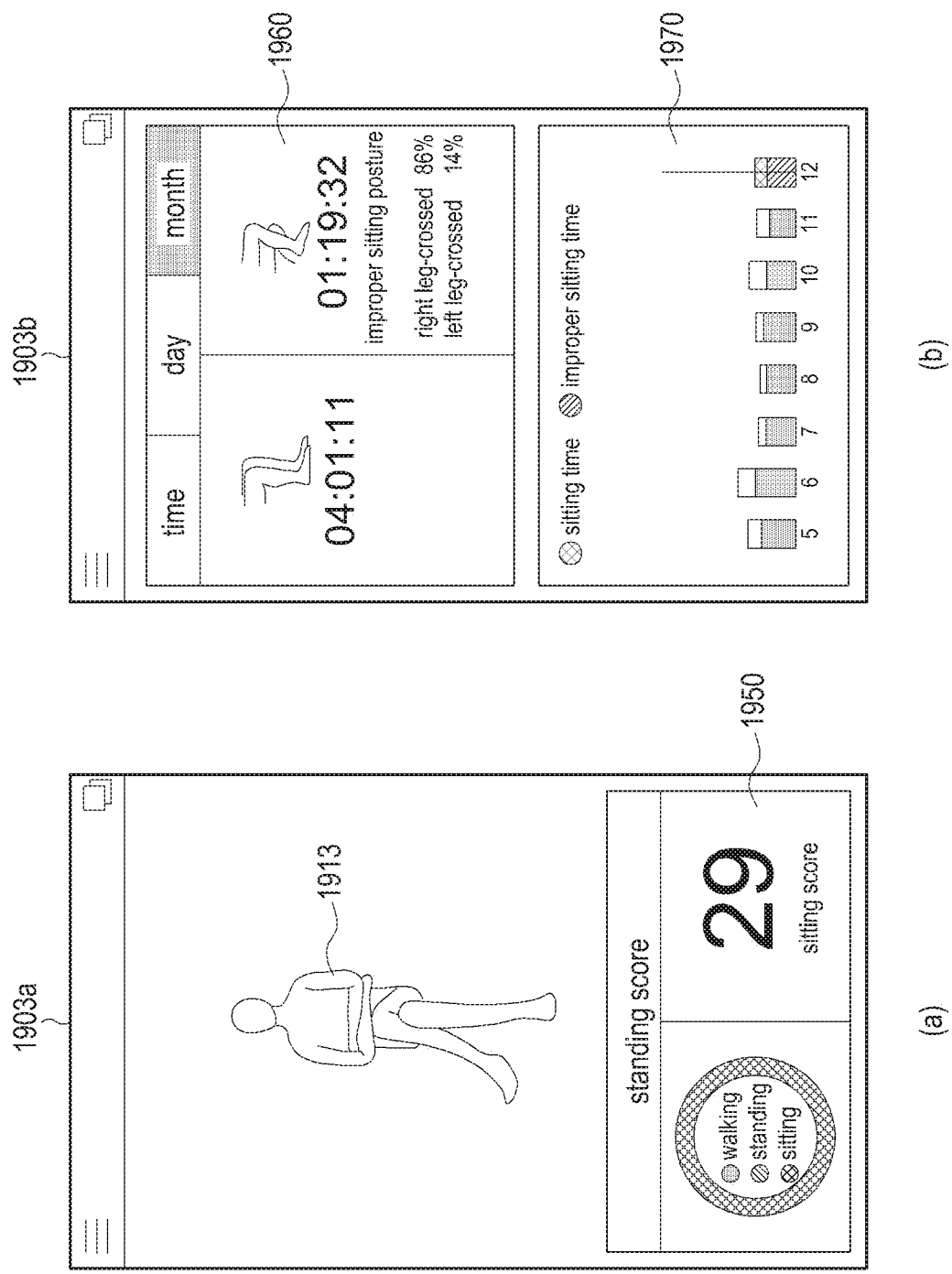

Referring to FIGS. 19C and 19D, screens 1903a and 1903b for outputting aggregate result information from information on the user's gait, which is accumulated for a certain time, may be provided. The output screen 1903a may display avatar information 1912 or 1913 on a representative figure of each posture, such as walking, sitting, or standing as the result accumulated for a certain time and score information 1950 indicating a state of each posture through a numerical value. Further, the output screen 1903b may display information 1960 indicating the number of times by which the user's posture, such as walking, sitting, or standing is normal and abnormal, a time, and a rate as the result accumulated for a certain time, such as time, day, and month, and information 1970 indicating the number of times by which each posture is normal or abnormal at each time zone through a graph. For example, in a case of the user's walking posture, avatar information 1912 on the representative figure of the user's walking posture and information 1950, 1960, and 1970 corresponding to the walking posture may be displayed as illustrated in FIG. 19C. In a case of the user's sitting posture, avatar information 1913 of the representative figure of the user's sitting posture and information 1950, 1960, and 1970 corresponding to the sitting posture may be displayed as illustrated in FIG. 19D.

Figure 20:
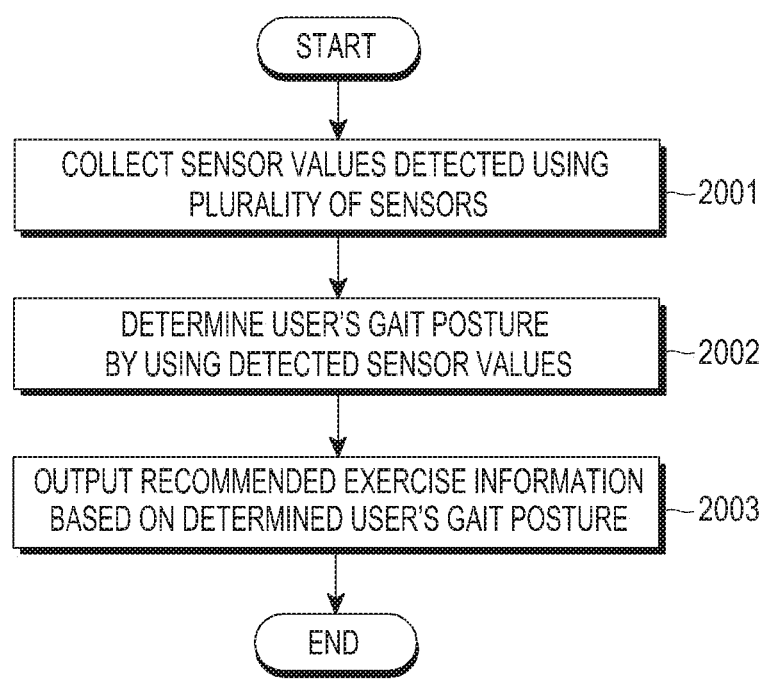
FIG. 20 is a flowchart illustrating a method of providing information based on a gait posture according to various embodiments of the present disclosure.
Figure 21:
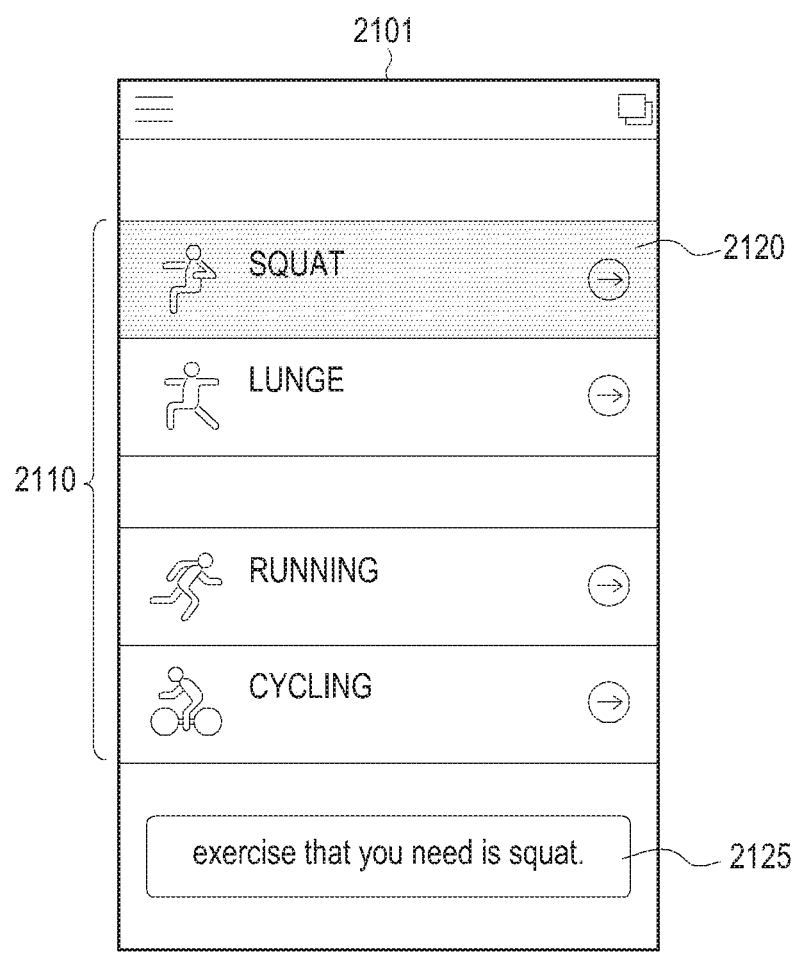
FIG. 21 is a view illustrating a screen for providing information according to a gait posture according to various embodiments of the present disclosure.

FIG. 20 is a flowchart illustrating a method of providing information based on a gait posture according to various embodiments of the present disclosure, and FIG. 21 illustrates a screen that provides information according to a gait posture according to various embodiments of the present disclosure.

The method of providing the information based on the gait posture according to an embodiment of the present disclosure will be described below in detail with reference to FIGS. 20 and 21.

Referring to FIG. 20, in operation 2001, the electronic device may collect sensor values detected using a plurality of sensors.

In operation 2002, the electronic device may determine a user's gait posture by using the detected sensor values.

In operation 2003, the electronic device may output information on a recommended exercise according to the user's gait based on the determined user's gait posture. When it is required to correct the posture based on the determined user's gait posture, the electronic device may recommend an exercise suitable for the correction of the posture. Further, the electronic device may recommend an exercise suitable for recovery of the fatigue according to the determined user's gait posture. In addition, the electronic device may recommend an exercise suitable for recovery of the accumulated fatigue of the user according to the gait.

Referring to FIG. 21, a screen 2101 for outputting information on the recommended exercise of the user's gait may display a recommended exercise list 2110 according to the user's gait posture and display an exercise, which is necessary based on the user's gait posture, with a color 2120 and text information 2125.

Figure 22:
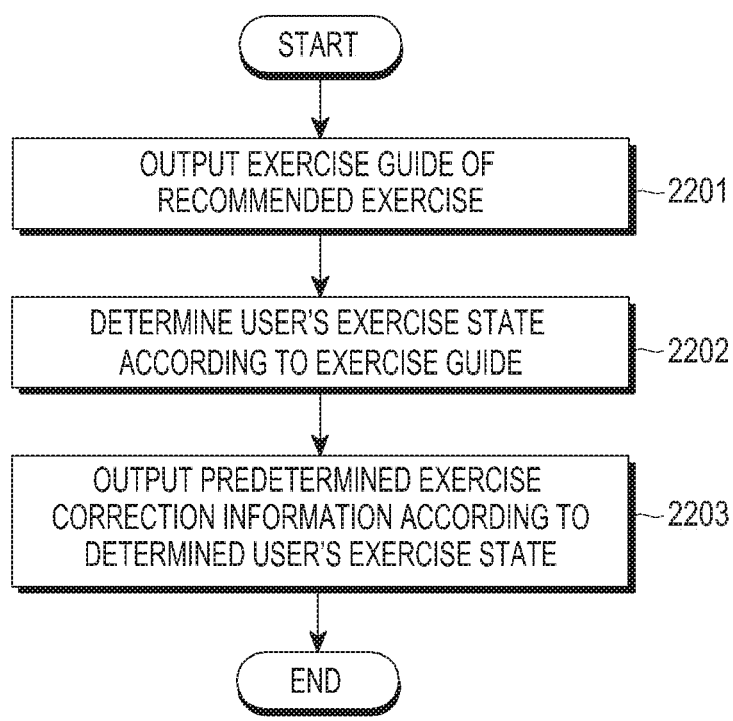
FIG. 22 is a flowchart illustrating a method of providing information based on a gait posture according to various embodiments of the present disclosure.
Figure 23A:
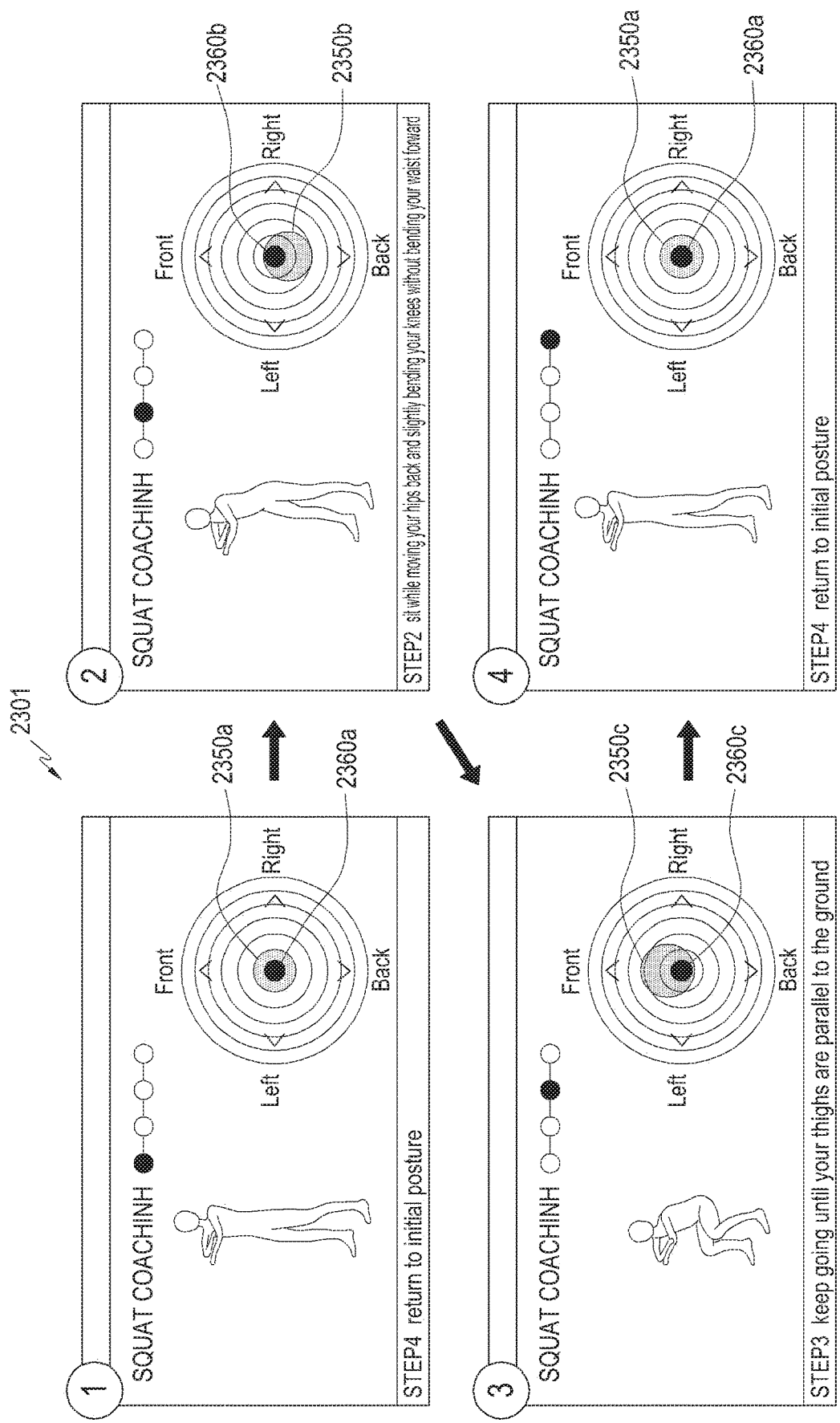
FIGS. 23A and 23B illustrate screens for providing information according to a gait posture according to various embodiments of the present disclosure.
Figure 23B:
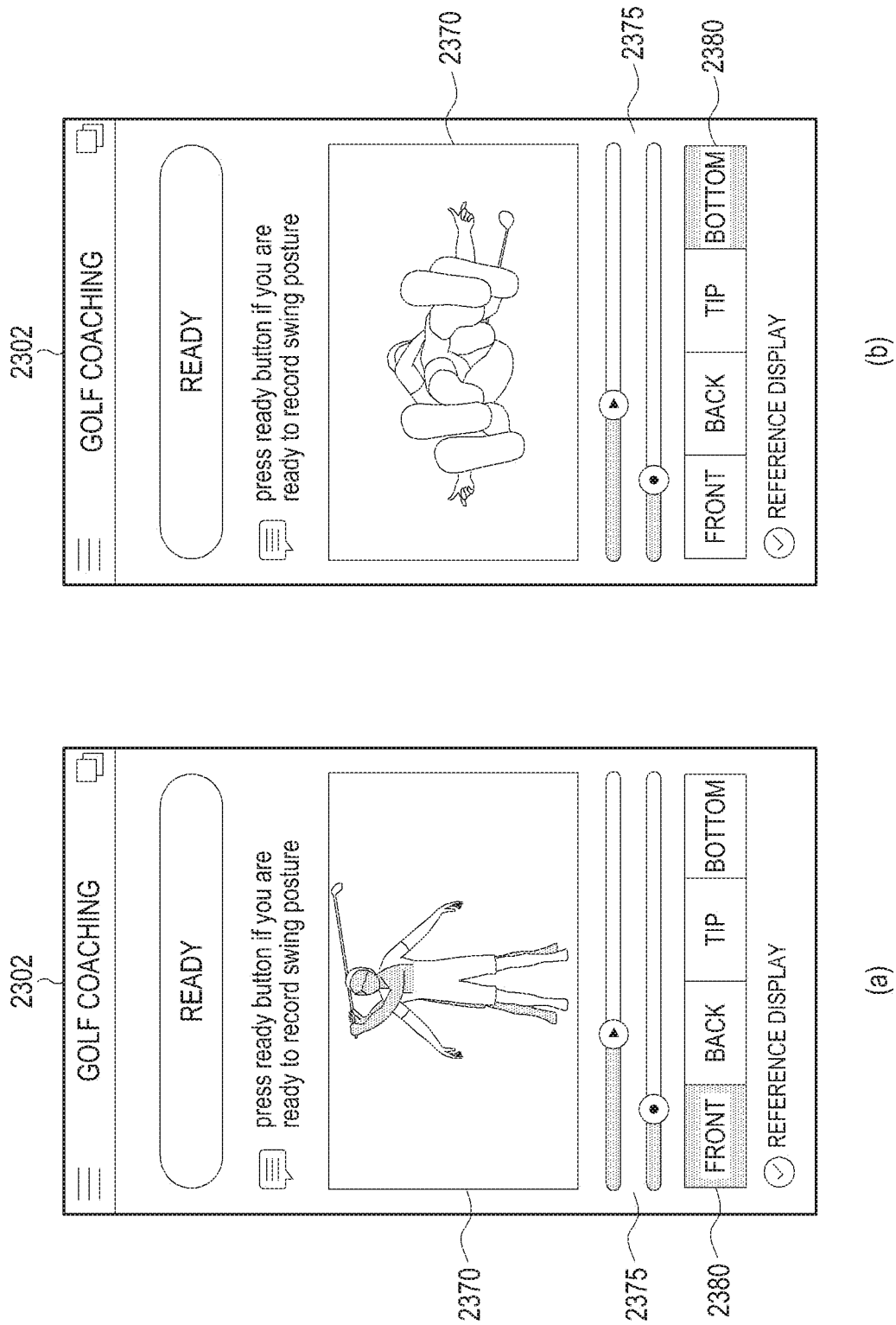

FIG. 22 is a flowchart illustrating a method of providing information based on a gait posture according to various embodiments of the present disclosure, and FIGS. 23A and 23B illustrate screens that provide information according to a gait posture according to various embodiments of the present disclosure.

The method of providing the information based on the gait posture according to an embodiment of the present disclosure will be described below in detail with reference to FIGS. 22 to 23B.

Referring to FIG. 22, in operation 2201, the electronic device may output an exercise guide of a recommended exercise according to the user's gait.

In operation 2202, the electronic device may determine an exercise state of the user who exercises according to the provided exercise guide.

In operation 2203, the electronic device may output certain exercise correction information according to the determined exercise state of the user. The exercise guide may coach the user in a proper exercise method of the exercise selected by the user through the information on the recommended exercise according to the user's gait based on the user's gait posture. The exercise guide may provide a guide of the reference COG preset for the proper COG according to the exercise and provide exercise correction information to make the COG of the user correspond to the guide of the COG.

Referring to FIG. 23A, on a screen 2301 for outputting the exercise guide of the exercise based on the recommended exercise of the user, an exercise method of each stage corresponding to actions which are divided from the exercise selected by the user is described through an avatar and text, and guides of the reference COG 2350a, 2350b, 2350c, and 2350d preset for the exercise actions of each stage and points of the COG 2360a, 2360b, 2360c, and 2360d of the user may be provided. For example, exercise posture correction information may be provided to place the points of the COG 2360a, 2360b, 2360c, and 2360d of the user at the guides of the reference COG 2350a, 2350b, 2350c, and 2350d.

Referring to FIG. 23B, a screen 2302 for outputting the exercise guide of the exercise (for example, golf) influenced by a location of the user's feet may display avatar information 2370 formalizing the posture of the exercise action, a button 2375 for selecting a location of the exercise action, and a button 2380 for selecting an eye direction of the avatar information. For example, the avatar information 2370 on the exercise action viewed from the front may be displayed as illustrated in FIG. 23B(a), and the avatar information 2370 of the exercise action viewed from the bottom may be displayed as illustrated in FIG. 23B(b). Further, the avatar information 2370 may visualize a feet's load distribution according to an exercise action by displaying a number, a color, or a contour in the part within which the load is distributed to make a difference according to a load level, so that the user can intuitively recognize the load of the correct exercise action. For example, in a golf swing, it is preferable that a load distribution of both feet is 50:50 in an address action, it is preferable that a load distribution of both feet is 65:35 in a top of backswing action, it is preferable that a load distribution of both feet is 35:65 in a downswing action, and it is preferable that a load distribution of both feet is 10:90 in a finish action. The load distribution of each action may be expressed through the avatar information 2370. With respect to a user's golf swing action, a load distribution according to an actual action of the user and a reference load distribution may be displayed in the form which can be intuitively recognized by the user.

FIGS. 24A to 24D illustrate a method of determining information based on a gait posture according to various embodiments of the present disclosure.

Figures 24A, 24B, 24C, 24D:
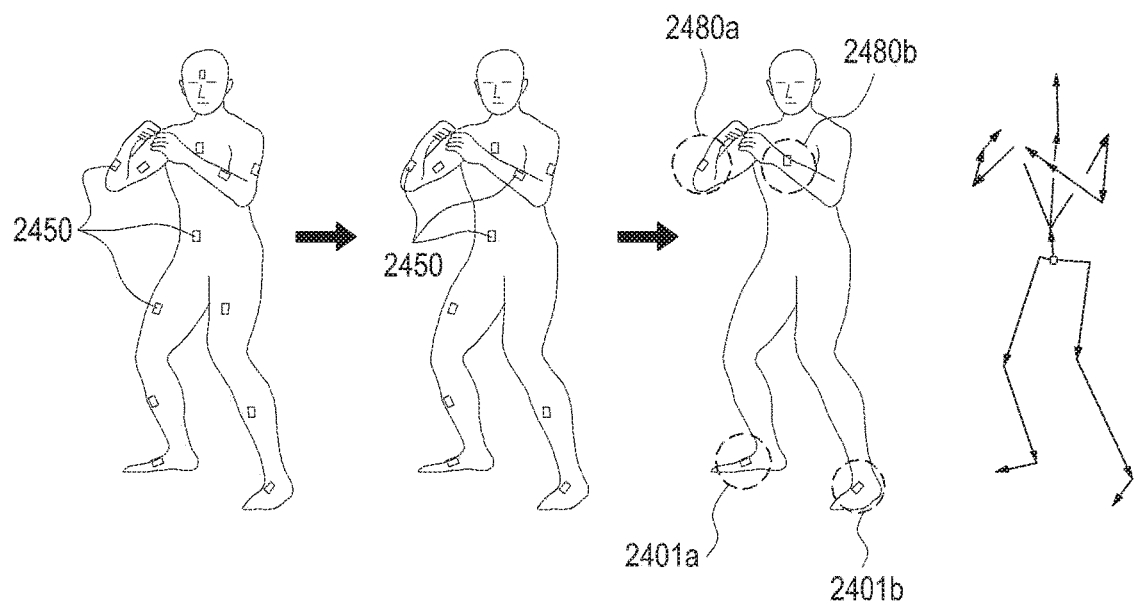
FIGS. 24A to 24D illustrate a method of determining information based on a gait posture according to various embodiments of the present disclosure.

Referring to FIGS. 24A to 24D, as information based on a gait posture according to various embodiments of the present disclosure, human body modeling information may be provided. The electronic device may determine a user's gait posture by using sensor values detected by a plurality of sensors, generate human body modeling information according to a user's motion based on the determined user's gait posture, and output the generated human body modeling information. To this end, the electronic device may collect an additional sensor value detected using an additional sensor located at another part, which is not the part around the user's sole and apply the additional sensor value to the user's gait posture so as to generate human body modeling information according to the a user's motion. The electronic device may construct a human body model in advance by using 13 sensors 2450 as illustrated in FIG. 24(a), and construct a human body model by using a smaller number of sensors, that is, 11 sensors 2450 through a kinematic analysis of the constructed human body model as illustrated in FIG. 24(b). Through such a process, the human body modeling information may be generated using electronic devices 2401a and 2401b and additional sensors 2480a and 2480b according to the present disclosure as illustrated in FIG. 24(c). For example, human body model data acquired using three sensors attached to the arm may be obtained through two sensors of the arm alone based on the human body model data acquired from the three sensors. Further, the human body modeling information is in the form of avatar information and may output, in real time, an avatar, which is generated by shaping a user's posture based on the generated human body modeling information, in the form of an image or a dynamic image.

FIGS. 25A to 25C illustrate screens for providing body information by using an electronic device according to various embodiments of the present disclosure.

Referring to FIGS. 25A to 25C, the electronic device, according to various embodiments of the present disclosure, may generate user's body information by using a plurality of sensors and output the generated body information. For example, in addition to a function of determining a user's gait posture through a plurality of sensors, the electronic device may further include various sensors for detecting user's body information (for example, a user's blood pressure, blood flow, heat rate, body temperature, respiration rate, heart and lung sound, EMG, ECG, and the like). The various sensors may include at least one of an HRV sensor, an HRM sensor, an EMG sensor, an EEG sensor, an ECG sensor, an IR sensor, and an E-nose sensor. Further, it is preferable that the various sensors are located around the user's feet, but the present disclosure is not limited thereto and may further include an additional sensor module located at another part (for example, a user's wrist, shoulder, chest, head, and the like) which is not the part around the user's feet. For example, as illustrated in FIGS. 25A to 25C, screens 2501a, 2501b, and 2501c for outputting user's body information may be provided. The output screen 2501a may display a button 2520 for measuring a weight in the user's body information as illustrated in FIG. 25(a). When the user selects the button 2520, the output screen 2501b may display user's avatar information 2510 and an operation for measuring the user's weight as illustrated in FIG. 25(b), and the output screen 2501c may finally display measurement result information 2520 on the user's weight as illustrated in FIG. 25(c). Although FIGS. 25A to 25C illustrate only an example of the measurement of the weight among the user's body information, the present disclosure is not limited thereto, and the user's blood pressure, blood flow, heart rate, body temperature, respiration rate, heart and lung sound, EMG, ECG, and the like, may be measured and displayed as various pieces of body information.

Figure 26:
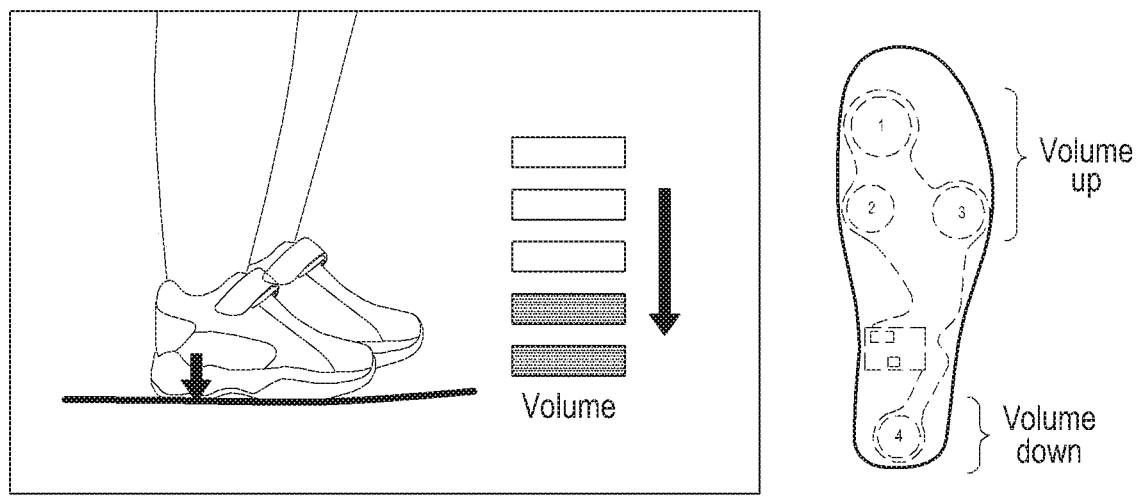
FIG. 26 illustrates a method of providing an interaction operation by using an electronic device according to various embodiments of the present disclosure.

FIG. 26 illustrates a method of providing an interaction operation by using an electronic device according to various embodiments of the present disclosure.

Referring to FIG. 26, the electronic device, according to various embodiments of the present disclosure, may extract an interaction command of the electronic device by using a plurality of sensors and may be controlled according to the extracted interaction command. For example, as illustrated in FIG. 26, the user's sole may be divided into a toe part and a heel part and sensor values acquired at the parts by the pressure sensors for detecting a change in the pressure of the user's sole applied to the ground are divided into volume up and volume down. When the sensor value is acquired at the heel part, the electronic device extracts an interaction command for making a volume down and control an operation for making the volume down according to the extracted interaction command. To this end, the electronic device may provide a setting function of extracting the interaction command by using the sensor values acquired from the plurality of sensors, and may extract an interaction command by using the sensor values acquired from the plurality of sensors according to the setting and may be controlled according to the extracted interaction command.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method of providing information according to a gait posture using an electronic device, the method comprising:
   collecting sensor values detected using a plurality of sensors located around a user's feet;
   determining a user's gait posture by using the detected sensor values; and
   outputting information on the user's gait posture, information on a recommended exercise for the user, information on joint fatigue of the user according to the gait based on the determined user's gait posture, and information on muscle fatigue of the user according to the gait,
   wherein the outputting of the information on the recommended exercise comprises outputting at least one of information on a recommended exercise for a correction of the user's gait posture, information on a recommended exercise for a recovery of the muscle fatigue of the user according to the gait, and information on a recommended exercise for a recovery of the joint fatigue of the user according to the gait based on the determined user's gait posture,
   wherein the outputting of the information on the muscle fatigue of the user according to the gait comprises:
      determining a user's gait period based on the determination of the user's gait posture,
      calculating a pressure change of the user's feet at a moment of landing according to the determined user's gait period,
      determining the joint fatigue of the user according to the gait based on the calculated pressure change at the moment of landing, and
      outputting information on the joint fatigue of the user according to the gait based on a result of the determination, and
   wherein the outputting of the information on the joint fatigue of the user comprises calculating a force applied to each joint by applying the calculated pressure change of the user's feet to predetermined dynamic human body modeling and determining the joint fatigue according to the calculated force applied to each joint.

2. The method of claim 1,
   wherein the plurality of sensors comprise a plurality of pressure sensors located at an insole of the user and an inertia sensor located around the user's feet, and
   wherein the inertia sensor comprise at least one of an acceleration sensor, a gyro sensor, and a geomagnetic sensor.

3. The method of claim 1, wherein the determining of the user's gait posture comprises determining the user's gait posture according to a detection order of the sensor values detected by the plurality of sensors.

4. The method of claim 1, wherein the determining of the user's gait posture comprises determining the user's gait posture according to a size of the sensor values detected by the plurality of sensors.

5. The method of claim 1, wherein the determining of the user's gait posture comprises:
   determining whether the user's gait posture corresponds to a state of at least one of walking, running, and being stopped by using the detected sensor values; and
   determining the user's gait posture according to the state.

6. The method of claim 1, wherein the determining of the user's gait posture comprises:
   determining a user's gait period by using the detected sensor values;
   calculating a gait posture determination factor including at least one of a pressure distribution change of the user's feet, an angle change of the user's feet, a change of the center of gravity of the user, the pressure change of the user's feet at the moment of landing, and an acceleration change of the user's feet during exercise according to the determined user's gait period; and
   determining the user's gait posture based on the calculated gait posture determination factor.

7. The method of claim 6, wherein the determining of the user's gait posture comprises comparing the calculated gait posture determination factor with a certain gait posture determination reference and determining the user's gait posture based on at least one of a type of the user's gait posture and a score generated by shaping a level of normality or abnormality of the user's gait posture according to a result of the comparison.

8. The method of claim 1, wherein the outputting of the information comprises outputting the information as at least one of visual, auditory, and audiovisual information.

9. The method of claim 1, wherein the outputting of the information on the user's gait posture comprises outputting in real time at least one of state notification information on the user's gait posture, avatar information formalizing the user's gait posture, and guide information according to the user's gait posture based on the determined user's gait posture.

10. The method of claim 9, wherein the outputting of the information on the user's gait posture comprises outputting a certain sound source according to the user's gait posture.

11. The method of claim 10, wherein the outputting of the information on the user's gait posture further comprises changing, when a separate sound source is reproduced in the electronic device, the reproduced sound source according to the user's gait posture and outputting the changed sound source.

12. The method of claim 1, wherein the outputting of the information on the muscle fatigue of the user according to the gait comprises:
   determining the user's gait period based on the determination of the user's gait posture, calculating an acceleration change of the user's feet during exercise according to the determined user's gait period, and determining the muscle fatigue of the user according to the gait based on the calculated acceleration change of the user's feet in the exercise; and
   outputting the information on the muscle fatigue of the user according to the gait based on a result of the determination.

13. The method of claim 12, wherein the determining of the muscle fatigue of the user according to the gait comprises calculating a reduced amount of the calculated acceleration change of the user's feet during exercise according to an elapse of the user's gait, and determining the muscle fatigue according to the calculated reduced amount.

14. The method of claim 1, wherein the outputting of the information on the recommended exercise of the user comprises outputting recommended exercise execution guide information on the recommended exercise information.

15. The method of claim 14, wherein the outputting of the recommended exercise execution guide information comprises:

outputting an exercise guide of the recommended exercise information;
determining an exercise state of the user according to the exercise guide; and
outputting certain exercise correction information according to the determined exercise state of the user.

16. The method of claim 1, wherein the plurality of sensors further comprise an additional sensor located at another part, which is not the part around the user's feet.

17. The method of claim 16, further comprising:
collecting an additional sensor value detected using the additional sensor;
generating human body modeling information according to a user's motion by applying the additional sensor value to the determination of the user's gait posture; and
outputting the generated human body modeling information.

18. The method of claim 1, further comprising:
generating human body information on the user by using the detected sensor values; and
outputting the generated human body information.

19. The method of claim 1, further comprising:
extracting an interaction command for the electronic device by using the detected sensor value; and
controlling the electronic device according to the extracted interaction command.

20. At least one non-transitory machine-readable storage medium for storing a computer program of instructions configured to be readable by at least one processor for instructing the at least one processor to execute a computer process for performing the method of claim 1.

21. An electronic device for providing information according to a gait posture, the electronic device comprising:
a pad part located at a user's sole;
a plurality of sensors located within the pad part; and
a controller configured to:
determine a user's gait posture by using detected sensor values, and
output information on the user's gait posture, information on a recommended exercise of the user, information on joint fatigue of the user according to the gait based on the determined user's gait posture, and information on muscle fatigue of the user according to the gait,
wherein the information on the recommended exercise comprises at least one of information on a recommended exercise for a correction of the user's gait posture, information on a recommended exercise for a recovery of the muscle fatigue of the user according to the gait, and information on a recommended exercise for a recovery of the joint fatigue of the user according to the gait based on the determined user's gait posture,
wherein the controller is further configured to determine a user's gait period based on the determination of the user's gait posture, calculate a pressure change of the user's feet at a moment of landing according to the determined user's gait period, determine the joint fatigue of the user according to the gait based on the calculated pressure change at the moment of landing, and control output of information on the joint fatigue of the user according to the gait based on a result of the determination, and
wherein the controller is configured to calculate a force applied to each joint by applying the calculated pressure change of a user's feet to predetermined dynamic human body modeling and determine the joint fatigue according to the calculated force applied to each joint.

22. The electronic device of claim 21, wherein the controller is further configured to:
collect sensor values detected using the plurality of sensors,
determine a user's gait posture by using the detected sensor values, and
output at least one of information on the user's gait posture, information on the muscle fatigue of the user according to the gait, information on the joint fatigue of the user according to the gait, and information on a recommended exercise of the user based on the determined user's gait posture.

23. The electronic device of claim 21, further comprising an external electronic device comprising:
a communication unit configured to receive the sensor values by using short range communication;
a controller configured to:
receive the sensor values detected using the plurality of sensors through the communication unit,
determine the user's gait posture by using the detected sensor values, and
output at least one of information on the user's gait posture, information on the muscle fatigue of the user according to the gait, information on the joint fatigue of the user according to the gait, and information on a recommended exercise for the user based on the determined user's gait posture; and
an output unit configured to output the information.

24. The electronic device of claim 21,
wherein the plurality of sensors comprise a plurality of pressure sensors located at the user's sole and an inertia sensor located around the user's feet, and
wherein the inertia sensor comprises at least one of an acceleration sensor, a gyro sensor, and a geomagnetic sensor.

25. The electronic device of claim 21, wherein the controller is further configured to determine the user's gait posture according to a detection order of the sensor values detected by the plurality of sensors.

26. The electronic device of claim 21, wherein the controller is further configured to determine the user's gait posture according to sizes of the sensor values detected by the plurality of sensors.

27. The electronic device of claim 21, wherein the controller is further configured to:
determine whether the user's gait posture corresponds to a state of at least one of walking, running, and being stopped by using the detected sensor values, and
determine the user's gait posture according to the state.

28. The electronic device of claim 21, wherein the controller is further configured to:
determine a user's gait period by using the detected sensor values,
calculate a gait posture determination factor including at least one of a pressure distribution change of the user's feet, an angle change of the user's feet, a change of the center of gravity of the user, the pressure change of the user's feet at the moment of landing, and an acceleration change of the user's feet during exercise according to the determined user's gait period, and
determine the user's gait posture based on the calculated gait posture determination factor.

29. The electronic device of claim 28, wherein the controller is further configured to:

compare the calculated gait posture determination factor with a certain gait posture determination reference, and determine the user's gait posture based on at least one of a type of the user's gait posture and a score generated by shaping a level of normality or abnormality of the user's gait posture according to a result of the comparison.

30. The electronic device of claim 21, wherein the controller is further configured to control output of the information as at least one of visual, auditory, and audiovisual information through an output unit.

31. The electronic device of claim 21, wherein the controller is further configured to control output, in real time, of at least one of state notification information on the user's gait posture, avatar information formalizing the user's gait posture, and guide information according to the user's gait posture based on the determined user's gait posture.

32. The electronic device of claim 31, wherein the controller is further configured to control output of a certain sound source according to the user's gait posture.

33. The electronic device of claim 32, wherein, when a separate sound source is reproduced in the electronic device, the controller is further configured to:

control changing of the reproduced sound source according to the user's gait posture, and control output of the changed sound source.

34. The electronic device of claim 21, wherein the controller is further configured to:

determine the user's gait period based on the determination of the user's gait posture, calculate an acceleration change of the user's feet during exercise according to the determined user's gait period, determine the muscle fatigue of the user according to the gait based on the calculated acceleration change of the user's feet during exercise, and control output of the information on the muscle fatigue of the user according to the gait based on a result of the determination.

35. The electronic device of claim 34, wherein the controller is further configured to:

calculate a reduced amount of the calculated acceleration change of the user's feet during exercise according to an elapse of the user's gait, and determine the muscle fatigue according to the calculated reduced amount.

36. The electronic device of claim 21, wherein the controller is further configured to control output of recommended exercise execution guide information on the recommended exercise information.

37. The electronic device of claim 36, wherein the controller is further configured to control:

output of an exercise guide of the recommended exercise information, determination of an exercise state of the user according to the exercise guide, and output of certain exercise correction information according to the determined exercise state of the user.

38. The electronic device of claim 21, wherein the plurality of sensors further comprise an additional sensor located at another part, which is not the part around the user's feet.

39. The electronic device of claim 38, wherein the controller is further configured to:

collect an additional sensor value detected using the additional sensor, generate human body modeling information according to a user's motion by applying the additional sensor value to the determination of the user's gait posture, and output the generated human body modeling information.

40. The electronic device of claim 21, wherein the controller is further configured to a control generation of human body information on the user by using the detected sensor values and control output of the generated human body information.

41. The electronic device of claim 21, wherein the controller is further configured to:

extract an interaction command for the electronic device by using the detected sensor value, and control the electronic device according to the extracted interaction command.

* * * * *